(12) United States Patent
Vilsmeier

(10) Patent No.: US 11,848,092 B2
(45) Date of Patent: *Dec. 19, 2023

(54) RADIOTHERAPY FEEDBACK DEVICE

(71) Applicant: Brainlab AG, Munich (DE)

(72) Inventor: Stefan Vilsmeier, Munich (DE)

(73) Assignee: BRAINLAB AG, Munich (DE)

(*) Notice: Subject to any disclaimer, the term of this patent is extended or adjusted under 35 U.S.C. 154(b) by 111 days.

This patent is subject to a terminal disclaimer.

(21) Appl. No.: 17/510,008

(22) Filed: Oct. 25, 2021

(65) Prior Publication Data

US 2022/0115110 A1   Apr. 14, 2022

Related U.S. Application Data

(60) Continuation of application No. 16/175,185, filed on Oct. 30, 2018, now Pat. No. 11,195,608, which is a division of application No. 15/713,201, filed on Sep. 22, 2017, now Pat. No. 10,143,855, which is a division of application No. 13/630,327, filed on Sep. 28, 2012, now abandoned.

(60) Provisional application No. 61/541,430, filed on Sep. 30, 2011.

(30) Foreign Application Priority Data

Sep. 30, 2011 (EP) ..................... 11183637

(51) Int. Cl.
G16H 20/40 (2018.01)
A61N 5/10 (2006.01)
A61B 34/10 (2016.01)
G16H 50/50 (2018.01)
G16H 10/60 (2018.01)
G16Z 99/00 (2019.01)

(52) U.S. Cl.
CPC ............ *G16H 20/40* (2018.01); *A61B 34/10* (2016.02); *A61N 5/1031* (2013.01); *A61N 5/1038* (2013.01); *A61N 5/1039* (2013.01); *G16H 10/60* (2018.01); *G16H 50/50* (2018.01); *G16Z 99/00* (2019.02); *A61B 2034/104* (2016.02); *A61B 2034/107* (2016.02)

(58) Field of Classification Search
CPC ...... A61B 34/10; A61B 2034/101–108; A61N 5/10–1084; A61N 2005/1085–1098
See application file for complete search history.

(56) References Cited

U.S. PATENT DOCUMENTS

2006/0271407 A1   11/2006   Rosenfeld et al.
2011/0052036 A1   3/2011    Valdivieso Cacique et al.

FOREIGN PATENT DOCUMENTS

EP   2189940   5/2010
EP   2189943   5/2010

*Primary Examiner* — Thaddeus B Cox
(74) *Attorney, Agent, or Firm* — Gray Ice Higdon

(57) ABSTRACT

A radiotherapy feedback device is provided which provides one of a plurality of indication signals for presentation to a surgeon based on the status of a current surgical procedure. In some aspects, an indication signal is provided to the surgeon if the surgical procedure on an anatomical structure is of sufficient status so as to respond well to subsequent radiotherapy.

22 Claims, 4 Drawing Sheets

RADIOTHERAPY FEEDBACK DEVICE

The present invention is directed to the (in particular automatic) assessment of a treatment plan (describing in particular a plan for performing a second treatment step to be performed after a first treatment step) and in particular to the use of such an assessment (in particular for finding the most suitable first treatment step allowing for the second treatment step to be performed in highest quality, in particular highest efficiency and/or safety). The present invention is directed to the medical field and in particular to the treatment of patients which is performed in accordance with the treatment plan. The present invention is in particular but not exclusively directed to the field of radiotherapy, in particular to the influence of surgical treatment or radiotherapy treatment.

Assessment of a treatment plan is a time-consuming and lengthy process. The object of the present invention is to provide an automatic assessment of a treatment plan.

The object is solved by the subject-matter of the independent claims. The dependent claims are directed to embodiments of advantage.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

Treatment in the present application refers to any kind of medical treatment, in particular pharmaceutical treatment, radiotherapy treatment, and surgical treatments. In particular, the treatment plan can be a radiotherapy treatment plan, a surgical treatment plan, or a pharmaceutical treatment plan which relates to a plan for medication of a patient. As a particular preferred embodiment, the present invention relates to the assessment of a radiotherapy treatment plan. A surgical treatment plan in particular relates to a planned sequence of surgical steps like a stepwise removal (resection) of parts of an anatomical structure of a patient. The term anatomical structure encompasses in particular healthy and pathological structures, like a healthy brain or a tumour.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The acquiring, determining and/or calculating steps described herein are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the World Wide Web (WWW). Such a cloud computer is located in a so-called cloud of computers which are all connected to the World Wide Web. Such an infrastructure is used for cloud computing which describes computation, software, data access and storage services that do not require end-user knowledge of physical location and configuration of the computer that delivers a specific service. In particular, the term "cloud" is used as a metaphor for the internet (World Wide Web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

Preferably, the inventive method is at least partly executed by a computer. That is, all steps or just some of the steps (i.e. less than a total number of steps) of the inventive method may be executed by a computer.

The invention is also directed to a program which, when running on a computer or when loaded onto a computer, causes the computer to perform the method steps of the method according to the invention and/or to a program storage medium on which the program is stored and/or to a computer on which the program is running or into the memory of which the program is loaded and/or to a signal wave, in particular a digital signal wave, carrying information which represents the program.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

As mentioned above, the present invention in particular relates to radiotherapy, in particular to a radiotherapy treatment plan. The radiotherapy treatment plan in particular describes at least partly an arrangement of treatment beams. That is the treatment plan comprises in particular complete information to define the arrangement of treatment beams or comprises incomplete information which describes some but not all parameters of the arrangement of treatment beams. Parameter can be at least some of the beam positions or angles. Even incomplete information can be used as a starting point for later planning and can be assessed in accordance with the criteria described herein. For instance, it can be assessed if an incomplete set of beam positions include beam positions which pass through a critical body part. Then, the corresponding treatment plan can be assessed to have negative quality (although the treatment plan describes the arrangement incomplete). The treatment beam and the arrangement of treatment beams will be described below. The radiotherapy is used for radiotherapy of a target region. The target region comprises or consists of a body part which is to be treated by the treatment radiation. This body part is referred to herein as "treatment body part". The treatment body part is in particular a tumour, in particular a tumour of which already a part has been resected by a surgical treatment. The present invention is in particular applied during surgery before or preferably after resection of this part.

The present invention relates to the field of medicine and in particular to the use of beams, in particular radiation beams, to treat parts of a patient's body, which are also called treatment beams. A treatment beam treats body parts which are to be treated, which are referred to in the following as "treatment body parts". These body parts are in particular parts of a patient's body, i.e. anatomical body parts. Ionising radiation is in particular used for the purpose of treatment. In particular, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation are X-rays, high-energy particles (high-energy particle beams) and/or ionizing radiation emitted from a radioactive element. The treatment radiation, in particular the treatment beam, is in particular used in radiation therapy or radiotherapy, in particular in the field of oncology. For treating cancer in particular, parts of the body comprising a pathologic structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

A treatment body part can be treated by one or more treatment beams issued from one or more directions at one or more times. Thus the treatment by means of the at least one treatment beam follows a spatial pattern and a time pattern. To cover the spatial and time features of the treatment by means of the at least one treatment beam, the term "beam arrangement" is used. The beam arrangement is an arrangement of at least one treatment beam.

The beam positions describe the positions of the treatment beams of the beam arrangement. The arrangement of beam positions is called positional arrangement. A beam position is preferably defined by the beam direction and additional information which allows to assign a specific location in in particular a three-dimensional space to the treatment beam, for example information about the coordinates in a defined coordinate system. The specific location is one point on preferably a straight line. This line is called "beam line" and runs in the beam direction and for instance runs along the central axis of the treatment beam. The defined coordinate system is preferably defined relative to the target region, but can also be defined relative to the treatment device or relative to at least part of the patient's body. The positional arrangement comprises (in particular consists of) at least one beam position, in particular a discrete set of beam positions (e.g. two or more different beam positions) or a continuous multiplicity (manifold) of beam positions.

During treatment, one or more treatment beams in particular adopts the treatment beam positions defined by the positional arrangement simultaneously or sequentially (the latter in particular in case there is just one beam source to emit a treatment beam). If there are several beam sources, at least a sub-set of all beam positions can also be adopted simultaneously by treatment beams during the treatment. In particular one or more sub-sets of the treatment beams can adopt the beam positions of the arrangement in accordance with a pre-defined sequence. A sub set of treatment beams comprises one or more treatment beams. The full set of treatment beams which comprise one or more treatment beams and which adopts all beam positions defined by the positional arrangement is the beam arrangement.

The data referred to herein as "patient data", in particular the candidate patient data, virtual patient data, current patient data, and reference patient data describe in particular medical information on the patient. This medical information can be any kind of information which is relevant for describing the medical status of the patient. The medical information is in particular generated by medical examination, in particular medical analysis and can be described by medical examination data, in particular medical analysis (e.g. a blood count). The result of a medical examination described by the medical examination data can be for instance age and gender of the patient or blood test results or medical history information (like previous medication, treatments, or tumour progression, etc.). The medical examination data comprises in particular imaging data which are generated by (medical) imaging methods. The imaging data in particular represent parts of the patient's body, in particular the target region (treatment body part). Imaging methods which can be used for generating the patient data are described below.

In the field of medicine, imaging methods (also referred to as "medical imaging methods") are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. However, some of the changes in the anatomical structure, in particular the pathological changes in the structures (tissue), may not be detectable and in particular may not be visible in the images generated by the imaging methods. A tumour for example represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MM scans when contrast agents are used to infiltrate the tumour. The MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernable in the image generated by the imaging method. In addition to these tumours, referred to as "enhancing" tumours, it is thought that approximately 10% of brain tumours are not discernable on a scan and are in particular not visible to a user looking at the images generated by the imaging method.

According to the present invention a data processing method is provided for determining an assessment of a candidate treatment plan. The assessment is in particular implemented by a mathematical expression (e.g. scalar value or vector or mathematical function, in particular distribution) which represents the quality (e.g. safety and/or effectiveness) of a candidate treatment plan. The assessment can in particular be a binary value representing acceptance or refusal of a candidate treatment plan or representing a score reflecting the quality of the treatment plan. The term "candidate" reflects in particular that treatment plan can be used for later treatment of the patient but has not to be used. Furthermore, the term "candidate" reflects in particular herein that the candidate is one of the plurality of possible candidates and in particular that an optional step refers to the selection of one of the candidates as a preferred solution. The selection is preferably performed based on an assessment. The assessment is preferably performed based on criteria.

The assessment describes in particular the quality of the candidate treatment plan. According to an embodiment of the invention, this quality is indicated to the user, in particular a surgeon. According to embodiments, the quality is determined based on the current patient data, i.e. the candidate patient data are the current patient data which describe the current medical status of the patient. In this way, the indication of the quality to the surgeon gives the surgeon a feedback whether the present status of surgery, in particular, present status of resection of tumour is already sufficient in order to achieve a radiotherapy treatment of sufficient quality. In particular, the determined quality is compared with a threshold in order to determine whether the quality is sufficient. Furthermore, an indication signal can be generated in order to indicate to the user, in particular surgeon that the required quality level is achieved. An indication signal herein is in particular an audio and/or visual and/or tactile indication signal.

In particular a plurality of candidate treatment plans are determined based on a plurality of (different) first virtual treatment steps. Based on a plurality of assessments for the plurality of candidate treatment plans, the best first virtual treatment step is determined and in particular indicated (e.g. proposed, displayed etc.) to the medical user.

Preferably, region data are acquired which describe a link between at least one region of the patient's body and the at least one first virtual treatment. In particular each of the at least one first regions represents a part of a tumour which is potentially resected by a surgical step, in particular virtually resected by a virtual surgical step. Preferably, the data processing method comprise an assignment step which assigns an assessment (in particular the quality described by the assessment) to the first virtual treatment which is the basis for the determined assessment. Then, preferably based on the at least one assignment for the at least one first virtual treatment and based on the region data, the quality of assessment is assigned respectively to the at least one region such that in particular for each region there is a quality value which describes the quality for a radiotherapy treatment if this region is resected (in a potential next surgical step). The at least one part can be in particular just one part which in particular corresponds to the remaining tumour, in particular to the remaining one or more elements of the tumour which still remained at the current stage of surgery. A part can be integral or can comprise spatially distinct elements. In particular by comparing the determined quality with the threshold, a region is determined to be preferred if the quality is above the threshold or is determined to be less preferred if the quality is below the threshold. Alternatively or additionally, the determined quality can be compared with the quality determined for the candidate treatment plan for treating the patient which is in the current status, i.e. which has been determined based on the current patient data. In this way the surgeon can check if any of the potential next surgical steps (first virtual treatment steps) results in an improvement of the quality of radiotherapy treatment.

Preferably, according to the invention candidate patient data are acquired. The candidate patient data describe medical information on the patient.

Furthermore, preferably data are acquired referred to as assessment criteria data. The assessment criteria data describe criteria for assessing a treatment plan to be assessed. The treatment plan to be assessed is referred herein as assessable treatment plan.

Furthermore and preferably in addition to the aforementioned acquiring steps, further data referred to as candidate treatment plan data are acquired. The candidate treatment plan data describe the candidate treatment plan.

Preferably the assessment of the candidate treatment plan is performed on the basis of the candidate patient data, the assessment criteria data and the candidate treatment plan data.

The treatment plan can cover different steps of treatment. The steps of treatment can be treatments of the same type (e.g. surgical steps of treatment) or can be of different type (e.g. medication steps, surgical step, and radiotherapy step). According to an embodiment of the present invention, the candidate patient data are virtual patient data (which are referred to as "virtual" since they are based on a simulation). The virtual patient data are preferably determined based on current patient data which describe the current medical information on the patient. In particular, the current medical information has been acquired recently (e.g. within less than one week, less than one day, less than one hour, or less than one minute). The current medical information has been in particular generated during a surgery during which the data processing method of the present invention is preferably performed.

Preferably the virtual patient data are determined by simulating a virtual first treatment of the patient. The virtual first treatment of the patient can be one of the abovementioned treatments (e.g. one or more a surgical step). In particular, the effect of the virtual (first) treatment of the patient on the current patient data is simulated in order to determine the virtual patient data.

According to an embodiment and as will be described below, the effect of a surgical step is simulated. In particular, the change of geometry of parts of the patient body due to the surgical step is simulated. The effect of this virtual treatment step (surgical step) on the current patient data (in particular image data describing the structure, in particular geometry of the patient's body) is simulated in order to determine the candidate patient data. In other words, the candidate patient data reflect the patient's body after performance of the virtual treatment step and are therefore referred to as virtual patient data. A virtual treatment step can comprise a plurality, in particular (consecutive) series of virtual treatment sub steps, which plurality (series) results in particular in a resection level (of tumour) and thus in the virtual patient data which represent the anatomical structure of the patient after the plurality of virtual treatment steps has been performed. According to another embodiment, the virtual patient data are determined for one or more of the plurality of virtual treatment sub steps and in particular the assessment is performed for one or more of the virtual sub steps.

There can be a sequence of consecutive treatments which are simulated. The treatments can be in particular of different type. According to an embodiment, there a plurality of first virtual treatments which in particular result automatically in second virtual treatments and optionally also automatically third or more virtual treatments. Thus there is a plurality of candidate paths respectively describing a sequence of first virtual treatment, second virtual treatment, and optionally third or more virtual treatments. In particular the plurality of first virtual treatments represent a set of predetermined first virtual treatments which can represent potential starting points for potential treatment paths. In particular at least one and preferably more of the following virtual treatments (for instance second virtual treatment and/or third virtual treatment) is determined by acquiring a candidate treatment plan based on the candidate patient data which result from the simulation of the previous treatment step.

According to the embodiments, a plurality of first virtual treatments are determined automatically based on at least one predefined first virtual treatment. In particular, a plurality of first virtual treatment steps are determined based on at least one predefined first treatment step. For instance, at least one boundary, preferably two boundaries are defined by the predefined first virtual treatment (in particular first predefined virtual treatment step). The boundaries define minimum and/or maximum limits for a region to be resected by resection steps (in accordance with the plurality of first virtual treatment steps). For instance, the predefined first virtual treatment can define a minimum amount of resection (e.g. 10%) and/or a surface which defines a boundary surface for a minimum resection. Furthermore, the predefined first virtual treatment can predefine a maximum amount of resection, e.g. 90% and/or define a maximum boundary, i.e. the surface which defines the boundary of maximum resection. Between the limits defined by the predefined first virtual treatment steps, a plurality of inbetween first virtual treatment steps can be automatically determined. The automatic determination can in particular based on an elastic fusion which elastically transforms the shape of the tumour defined by the minimum boundary surface into the shape of tumour defined by the maximum boundary surface. There can be a predefined number of intermediate steps which are automatically determined by the aforementioned elastic fusion, in particular by interpolation between the minimum boundary and the maximum boundary. In this way, an automatic generation of the starting points can be performed.

In particular, the determined candidate treatment plan describes the treatment plan for the second treatment step (in particular second virtual treatment step) which is to be performed after the first treatment step was performed.

Preferably, the most suitable first virtual treatment (step) is determined on the basis of the assessments of the consecutive virtual treatments (steps). Alternatively or additionally first virtual treatment steps which result in a negative assessment of the corresponding candidate treatment plan for the second treatment step are determined (and in particular indicated to the user).

In particular, the first virtual treatment is a surgical step and the second virtual treatment is a radiotherapy treatment step.

As mentioned above, the candidate treatment plan is preferably assessed. According to a preferred embodiment the assessment of the candidate treatment plan is indicated to a user (in particular medical doctor, in particular surgeon). In particular, the data processing method received input data describing a first virtual treatment step, in particular a plurality of first virtual treatment steps (e.g. from a user or navigation system which detects positions of e.g. a pointer). Preferably, the data processing method outputs assessments of a plurality of candidate treatment plans which result for each of the plurality of input virtual first treatment steps.

According to an embodiment and as mentioned above, there is the plurality of first virtual treatment steps. For each of the plurality of first treatment steps, a candidate treatment plan for the second step is determined. The candidate treatment plan for the second step describes a plan for performing the second virtual treatment step. The treatment plan is preferably but not obligatory automatically assessed. Preferably such an assessment is performed for all of the automatically determined second virtual treatment steps. In this way, that one of the first virtual treatment steps can then be selected as a recommendation for the user for which a second virtual treatment step has been determined which resulted in the best assessment (e.g. which has the highest score reflected by the assessment).

According to a preferred embodiment, the treatment plan described by the candidate treatment plan data is a plan for a radiotherapy treatment. Preferably, the radiotherapy treatment is planned to be performed for treating a target region of the patient. Preferably, the candidate treatment plan is a plan for radiotherapy treatment of a target region of the patient's body. The target region including in particular the treatment body part which is preferably treated by the radiotherapy treatment.

The candidate patient data comprise preferably information on the candidate target region, in particular information on the treatment body part. This information describes in particular the geometry and/or position of the target region. The term geometry covers herein size and/or shape and/or volume of the target region.

Target region information in particular comprises categories of information which relate to the geometry, position or pathologic state of the target region. The term of geometry in this context encompasses for example the shape (for example similarity to a basic geometric shape such as a sphere or a box) or dimension (length, diameter, radius or circumference) of the target region. The position of the target region is in particular described by its position relative to other parts of the patient's body or relative to the treatment device in the context of this disclosure, a treatment device is the device used for emitting the treatment beam such as an x-ray tube, particle accelerator or radioactive substance. The pathologic state of the target region is in particular described by the kind of disease (more particularly, the type of tumour) or injury which is present in the target region. Additionally, the pathologic state may be described by the history of the disease or injury such as the geometry or the position of the target region at a previous point in time. The geometry of a target region may also be described by the volume or the two-dimensional area (both volume and area are also referred to as size) covered by the target region in a cross section or specific perspective.

Preferably, the candidate patient data describe the anatomical structure of at least part of the patient's body. Those parts include in particular the treatment body part and/or parts outside the treatment body part (outside body parts). The outside body parts can be critical body parts or non-critical body parts. According to an embodiment, the geometry and/or position of the target region, in particular the treatment body part is determined based on information on the geometry and/or position of outside body parts and/or the geometry and/or position of one of the outside body parts is determined based on the geometry and/or position of other ones of the outside body parts and/or the treatment part. This procedure is in particular of advantage if one of the body parts is not visible in the image data generated by the imaging methods. In this case, the geometry and/or position of the invisible body part can be in particular derived from information of the visible body parts.

According to an embodiment, only Mill data described by the candidate patient data are used for determining the candidate treatment plan.

In the following, the step of determining the assessment is described in more detail.

As mentioned above, assessment criteria data are acquired. Preferably, the assessment criteria data describe at least one approval template which describes the criteria for assessing the assessable treatment plan. The criteria comprise in particular criteria for acceptance and/or rejection of the accessible treatment plan.

According to an embodiment, the criteria comprise predetermined criteria and/or criteria determined based on the candidate patient data. In particular, the criteria are flexible adapted in dependence on the candidate patient data in order to find the best suitable criteria which are applicable for the assessment of the treatment plan for the present patient. For instance, data describing a table (which links patient data with the criteria) are provided. Depending on the patient data, those criteria are selected which are linked in accordance with the table. For instance, different criteria can be applied in dependence on the status of progression of a tumour. The status of progression is described by the candidate patient data. The criteria may for instance also depend on the age of the patient. For instance, criteria describing a dose limit for parts of the body may depend on age of the patient and/or progression of the tumour. The criteria can be based on tumour grades, ICD-9 classification, Simpson grade, oxygenation of tumour, degree of metastasis of tumour, blood count values, tumour indicator values, like PSA value.

According to a further embodiment the assessment criteria data comprise the description of criteria which are assigned to reference patient data. In particular, there is a plurality of reference patient data and the respective ones of the plurality of reference patient data are assigned to respective criteria. Preferably a determination of the criteria is performed based on a similarity measure which describes the similarity between the candidate patient data and the respective ones of the plurality of reference patient data. Preferably that one of the reference patient data is selected for which the similarity measure shows the highest degree of similarity. The similarity measure is preferably performed by comparing the candidate patient data with the reference patient data. Preferably, the criteria used for the assessment are the criteria which are assigned to the selected one of the reference patient data (i.e. the reference patient data which are most similar to the candidate patient data).

As mentioned above, the criteria, in particular the approval template is adapted in dependence on the candidate patient data. To this end, for instance, intermediate values not included in the above-mentioned criteria table are determined based on the candidate patient data. For instance if a dose limit is described for a patient age of 60 and another dose limit is described for a patient age of 65 and the candidate patient data describe a patient age of 63, a linear interpolation between the dose limit for 60 and the dose limit for 65 can lead to the dose limit used as a criteria for assessing the candidate treatment plan for the present patient.

The criteria can be criteria for the required coverage of the target region (e.g. a conformity index). The criteria can describe a required equal distribution of the doses in the outside body parts which outside body parts in particular do not include critical body parts. Critical body parts are outside body parts for which the dose should not exceed an upper limit in order to assure that essential body functions are not affected. An example for a critical body part is the visual center in the brain.

According to a preferred embodiment, the criteria include a description of a minimum dose which is to be applied to the target region. According to a further embodiment, the criteria include a maximum dose which is the highest dose to be acceptable for critical body parts.

According to a preferred embodiment, the assessment criteria data, in particular the approval template describes a dose distribution and criteria according to which a deviation from the dose distribution is not allowed or only allowed within a predefined limit or in accordance with predefined rules. In particular, the deviation from the required dose distribution may be described as a distortion which may not exceed a pre-defined threshold.

Preferably, the criteria are set independently for the level of under dosage within the target volume, the maximum dose around the tumour, and/or the maximum dose for each critical structure.

According to a further embodiment, there is a plurality of criteria described by the assessment criteria data. Preferably, the different criteria are weighted. The weighing allows to determine more or less important criteria. The weighing can be performed by using a balanced score card.

According to another embodiment, dose distribution data are acquired which describe the dose distribution within the patient's body if a radiotherapy treatment is performed in accordance with the candidate treatment plan. Preferably, the acquired assessment criteria comprise criteria for the dose distribution. Preferably, the determining of the assessment is based on the dose distribution described by the dose distribution data. Preferably, the dose distribution data are received as predetermined dose distribution data or are determined based on the treatment beam absorption data (mentioned below) and the candidate treatment plan.

Preferably, treatment beam absorption data are provided which describe the absorption properties of the at least part of the body, in particular the (different) absorption properties for different elements (referred to as "body elements") of the at least part of the body and/or the relative position of these different elements of the at least part of the body. The absorption properties describe in particular the percentage of the energy of the treatment beam which is absorbed by one of the respective body elements per unit volume, in particular as a function of the energy level of the treatment beam. Examples of body elements include in particular the treatment body part and the outside body part. The absorption data describe in particular the absorption properties of the body elements with respect to the treatment radiation, in particular the position and/or geometry (size and/or shape) of the at least part of the body (to be treated by the radiation) and in particular of the different elements (like elements of a bone structure or elements of a fat structure). For instance the absorption of fat is less than the absorption of bone.

The treatment beam absorption data can be provided in different ways. The image data included in the candidate patient data can be used to determine the treatment beam absorption data. Databases can also be used to determine the treatment beam absorption data. Absorption properties of different body elements are for example stored in the database, and the different absorption properties are assigned to the different body elements described by the pre-optimisation image data. To this end, the regions shown by the image data described by the candidate patient data are for example segmented and identified as respectively representing a particular body element. A particular absorption property is stored in the database for each of the particular body elements and retrieved by the method according to the invention. It is thus possible to simulate the at least one treatment beam passing through the body (and thus through the body elements) and the treatment beam energy being absorbed by the body (and thus by the different body elements), and expected dose data for the body (and in particular for the different body elements) can be calculated.

According to another embodiment, treatment beam absorption data are determined from the reference patient data which are most similar to the candidate patient data, in particular wherein for the determination a statistical processing of the reference patient data is performed. Preferably, the dose distribution data are determined based on the treatment beam absorption data and the candidate treatment plan.

The candidate treatment plan in particular describes the relative position between the target region and the arrangement of treatment beams and in particular the energies of the treatment beams of the arrangement. According to another embodiment, dose distributions (referred to as "comparison dose distributions") for reference patients referred to as "comparison patients" which have been treated (or the treatment of which as been simulated) in accordance with treatment plans referred to as "comparison treatment plans" are acquired and the comparison dose distribution is adapted (for instance by using image fusion) to the dose distribution to be expected for the patient based on the candidate patient data. The term "image fusion" is explained later. The set of comparison patients can comprise or consist of at least part of the reference patients mentioned above. In particular, the comparison treatment plans can comprise or consist of at least parts of the reference treatment plans mentioned herein. Preferably, a similarity measure is determined which describes similarity between the candidate patient data and patient data of the comparison patients (referred to as comparison patient data). This similarity measure is called patient similarity measure. Preferably, a similarity measure between the candidate treatment plan and the comparison treatment plans is determined for the respective comparison treatment plans. This similarity measure is called planned similarity measure. Preferably based on at least one of planned similarity measure and patient similarity measure a comparison dose distribution is selected which is assigned to at least one of the most similar comparison treatment plan or the most similar comparison patient. The selected comparison dose distribution is assumed to represent the dose distribution within the patient's body after performing the radiotherapy treatment in accordance with the candidate treatment plan. Preferably, the fulfillment of the criteria is decided based on this dose distribution.

The above-mentioned treatment beam absorption data allow to determine the dose distribution and thus to determine whether the above-mentioned criteria (which relate to the dose) are met or not.

The treatment beam absorption data can in particular be determined based on image data which are generated using a computer tomographic analysis method. The CT image is preferably described by the candidate patient data. The CT image represents in particular the density of elements of the patient's body (referred to as body elements). The absorption properties of the body can be calculated based on the density of the body elements.

To this end, preferably an intensity value is calculated for each voxel of the CT image. The intensity value characterizes the attenuation (in particular absorption) of the x-ray radiation by the body elements. The attenuation is preferably described by a so called CT value which is preferably described in Hounsfield units. That is, the CT image data preferably describe CT-values for the voxels of the CT image. Preferably, the CT-values are assumed to correspond to the absorption properties of the voxels which can be part of the body elements. In particular a linear relationship between the CT-values and the absorption properties is assumed. In order to present a processed CT image to a user, the planning image data are often processed in order to reflect a sub range of the full range of CT-values by brightness values of the processed image. This processing is also called "windowing". As far as herein the term "CT image" is used, it preferably refers to an image which represents the CT values of the voxels and preferably does not refer to the processed CT-image (e.g. processed by "windowing").

According to a further embodiment, the criteria describe a target dose volume histogram, i.e. a target DVH. Preferably, a DVH is calculated based on the treatment beam absorption data and compared with the target DVH in order to determine whether the criterion is fulfilled or not.

In this application, the term "image morphing" is also used as an alternative to the term "image fusion", but with the same meaning.

Elastic fusion transformations (e.g. image fusion transformation) are in particular designed to enable a seamless transition from one data set (e.g. first data set, e.g. first image) to another data set (e.g. second data set, e.g. second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $1/10$ or $1/100$ or $1/1000$ of the diameter of the image, and in particular about equal to or less than the distance between neighbouring voxels. Due in particular to a high number of (iteration) steps, large deformations can be implemented.

The determined elastic fusion transformation can be in particular used to determine a degree of similarity (similarity measure also referred to as "measure of similarity") between the first and second data set (first and second image). To this end, the deviation of the elastic fusion transformation and an identity transformation is determined. The degree of deviations can be for instance calculated by determining the difference between the determinant of the elastic fusion transformation and the identity transformation. The higher the deviation is the less is the similarity. Thus, the degree of deviation can be used to determine a measure of similarity.

A measure of similarity can in particular be determined on the basis of a determined correlation between the first and second data set.

The candidate treatment plan can be received from the user. In particular, the received candidate treatment plan has been adapted to fit to the patient, in particular the candidate patient data. According to a further embodiment which is described in more detail in a section below entitled "automatic treatment planning method", the candidate treatment plan is determined automatically. The candidate treatment plan can be determined as described in this section in the same manner as it is described there for the determination of the "current treatment plan data". In particular the step of acquiring the candidate treatment plan data can be performed in the same manner as the step of acquiring the current treatment plan data as described in the below section entitled "automatic treatment planning method".

As described in this section, the current treatment plan data is determined on the basis of the current patient data. Correspondingly, the candidate treatment plan is determined based on the candidate patient data. In other words, the current patient data described in the section below has to be understood as an example for the candidate patient data.

The target region described by the candidate patient data is also referred to herein as "candidate target region". The body of the patient described by the candidate patient data is also referred to herein as "candidate patient's body".

The determined assessment is preferably indicated to the user. To this end, preferably indication information is determined. The indication information can for instance be indicated to the user by generating an indication signal which represents the indication information. The indication information describes in particular the determined assessment and/or qualifies first virtual treatment steps (see below), in particular qualifies a surgical treatment step (like a resection of part of a tumour).

As mentioned above, the best virtual treatment (e.g. most suitable first treatment step) can be determined according to one of the embodiments of the invention. This best virtual treatment is preferably indicated to the user based on indication information. The indication information is in particular indicated to the user by using an indication signal.

According to a further embodiment, a plurality of virtual surgical treatment steps are determined which result in a negative assessment of the candidate (radiotherapy) treatment plans which result from the determination of the candidate patient data based on the virtual surgical treatment step. In particular at least one less-preferred or "forbidden" region within the patient can be determined based on the determined virtual surgical treatment steps which would result in negative conditions for radiotherapy treatment, i.e. for which the determined candidate treatment plans would have a negative assessment. In particular the one or more regions are scored in accordance with the score described by the assessment. Based on this, at least one less-preferred or forbidden regions can be determined within the patient's body. The regions can in particular be clusters of subregions which subregions represent in particular parts of the tumour which in particular still remained at the present stage of procedure.

Based on the acquired instrument data which describe the position of an instrument used for a surgical step, indication information, in particular indication signal can be determined and in particular generated in order to warn the surgeon that he is close to a less-preferred or "forbidden" region. The instrument data can in particular be generated by using a navigation system for navigating the surgical instrument which detects the position of the instrument. The navigation system in particular determines, in particular detects the relative position between the surgical instrument and the patient's body, in particular the target region. In particular, a map can be generated which shows the less-preferred or forbidden regions to the surgeon for instance by displaying those regions in an optical instrument (lens or microscope) used by the surgeon for treatment of the target region. The navigation system in particular comprises the aforementioned computer to perform the method steps of one of the methods described herein.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU), a working memory, advantageously an indicating device for issuing an indication signal (for example, a visual indicating device such as a monitor and/or an audio indicating device such as a loudspeaker and/or a tactile indicating device such as a vibrator) and advantageously a permanent data memory, wherein the data processing device processes navigation data forwarded to it by the receiver and can advantageously output guidance information to a user via the indicating device. The navigation data can be stored in the permanent data memory and for example compared with data stored in said memory beforehand It is the function of a marker to be detected by a marker detection device (for example, a camera or an ultrasound receiver), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or one or more (individual) markers in a predetermined spatial relationship. A marker device comprises one, two, three or more markers in a predetermined spatial relationship. This predetermined spatial relationship is in particular known to a navigation system and for example stored in a computer of the navigation system.

A pointer is a rod which comprises one or more—advantageously, two—markers fastened to it and can be used to measure off individual co-ordinates, in particular spatial co-ordinates (i.e. three-dimensional co-ordinates), on a part of the body within the framework of a morphing method, wherein a user guides the pointer (in particular, a part of the pointer which has a defined and advantageously fixed location with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off coordinates (in particular, the tip of the pointer) is in particular known. The surgical navigation system then enables the location (of the three-dimensional co-ordinates) to be assigned to a predetermined body structure, wherein the assignment can be made automatically or by user intervention.

Of course it is also possible to additionally or alternatively determine preferred regions which, if removed in a surgical step, would result in a candidate target region which in turn would result in a candidate treatment plan for which an acceptable assessment is determined according to the method of the present invention.

To this end, the assessment is preferably determined for a plurality of virtual surgical steps. The virtual surgical steps are in particular steps which represent the resection of a part of the target region, in particular the current target region. In this way, the above-mentioned map can be generated which describes the one or more regions (which can be resected by the virtual surgical step) either as preferably to be resected or non-preferably to be resected based on the determined assessment (which is determined for the respective virtual surgical steps).

According to preferred embodiments, the automatically generated assessments are used in order to give indication whether a further resection leads to a better result of the radiotherapy treatment as can be already achieved with the current situation. In particular, one or more assessments for one or more virtual surgical steps which virtually result in at least part of the remaining tumour (in particular resection of the total remaining tumour) are determined. The current situation is described by the current patient data. For the current patient data also an assessment (referred to as current assessment) is performed. This current assessment is preferably compared with aforementioned assessments which reflect the one or more virtual surgical steps (those assessments are referred to as virtual assessments). If the one or more virtual assessments are indicating better quality than the current assessment and/or if the current assessments indicate better quality than the one or more virtual assessments, this is preferably determined and a corresponding indication information is preferably also determined and in particular a corresponding indication signal representing the indication information is issued to the user (in particular surgeon).

The present invention is in particular directed to provide a process to determine the extent of surgery based on an instant radio surgery feasibility assessment.

The present invention has in particular the following background:

Surgeons struggle to determine the extent of surgery, and typically make the decision based on balancing the desire to resect as much as possible while keeping the risk of complications under control. Since this results most of the times is subtotal resection, other treatments may be required at some point in time. Radiosurgery seems to provide advantages if applied within a few days following surgery. This invention covers a process suitable to determine the extent of surgery based on an assessment if Radiosurgery of the remaining structure is feasible, i.e. safe and effective based on current knowledge/best practice.

The present invention is in particular directed to the following embodiments:

A A process for deciding the extent of surgery comprising the following steps. Simulating various options of surgery covering various alternatives regarding extent and location of resection, using an automated planning process for generating a complete or at least partial treatment plan, assess safety and/or effectiveness of the various plans, and select the option of surgery most desirable based on such analysis.

A1 A process where the treatment plan is generated using a plan template.

A2 A process where the same template may be applied to multiple options of surgery using elastic fusion.

A3 A process where the treatment plan is based on MM data only.

A4 A process where the dose absorption is calculated based on a statistical model correlated to the specific patient using elastic fusion.

A5 A process where the treatment plan is calculated on a cloud server.

A6 A process where the criteria for accepting and/or rejecting a treatment plan are part of the treatment plan template or derived on certain criteria from a database.

B A process for combining two or more consecutive treatments, comprising several iterations of simulating prior to and multiple times during the current treatment the implications for the next treatment, with the goal of improving the start point of the following treatment.

C A process for deciding the extent of surgery comprising the following steps: Generating a diagnostic examination providing sufficient 3D data to capture the current extent of surgery, deploy an automated planning process for generating a complete or at least partial treatment plan, assess safety and/or effectiveness of that plan, and decide whether to continue with surgery based on such analysis.

C1 A process where the treatment plan is generated using a plan template

C2 A process where a previously generated plan may be adopted instead of such template using elastic fusion C3 A process where the extent of surgery, if not directly visible, may be derived as a result of an elastic fusion based on other surrounding structures that are visible.

C4 A process using video-streaming through the internet with state-of-the-art compression algorithms based on changes in image content to display the result of the analysis at an end device.

C5 A process where the number of interpolated images between each pair of exams are determined based on the time interval between each exam to result in a linear time line over the entire range of exams.

PART 1 OF AUTOMATIC TREATMENT PLANNING METHOD

The present invention is also directed to a treatment planning method, in particular, a method of (automatically) determining a treatment plan using data processing techniques.

Planning a treatment, in particular a radiotherapy treatment, typically is a time-consuming and lengthy process which is normally performed by a medical physicist. This invention eliminates treatment planning as a manual process by proposing a method of automatic treatment planning and provides the advantage of adapting a predetermined treatment plan to a current anatomical situation, in particular in case new 3D anatomical information about the patient's body is available. This is in particular necessary if the precise position of for example organs in the interior of a patient's body is not known due to movement of the organs when placing the patient onto a bed for radiotherapy treatment or due for example the varying spatial extent of other organs, such as the urinary bladder which depends on the level of fluid held by the bladder. In that case, it is necessary to adapt a predetermined geometry of treatment beams to the current position of the target region (which is meant to be irradiated with the treatment beams) relative to the rest of the patient's body or to the treatment device.

The movements of the treatment body parts are in particular due to movements which are referred to in the following as "vital movements". Reference is also made in this respect to the above-mentioned applications EP 08 169 422.6 and EP 09 160 153.4, which discuss these vital movements in detail. In order to determine the position of the treatment body parts, analytical devices such as x-ray devices (in particular cone beam CT—CBCT devices), CT devices or MRT devices are used to generate analytical images (such as x-ray images or MRT images) of the body. Analytical devices are in particular devices for analysing a patient's body, for instance by using waves and/or radiation and/or energy beams, in particular electromagnetic waves and/or radiation, ultrasound waves and/or particles beams. Analytical devices are in particular devices which generate images (for example, two-dimensional or three-dimensional images) of the patient's body (in particular, internal structures and/or anatomical parts of the patient's body) by analysing the body. Analytical devices are in particular used in medical diagnosis, in particular in radiology. However, it can be difficult to identify the treatment body part within the analytical image. It can in particular be easier to identify an indicator body part which correlates with changes in the position of the treatment body part and in particular the movement of the treatment body part. Thus, tracking an indicator body part allows a movement of the treatment body part to be tracked on the basis of a known correlation between the changes in the position (in particular the movements) of the indicator body part and the treatment body part.

Preferably, the inventive method is at least partly executed by a computer. That is, all steps or just some of the steps (i.e. less than a total number of steps) of the inventive method may be executed by a computer.

The inventive method preferably is a data processing method and constitutes a method of determining a treatment plan. A treatment plan preferably describes a medical treatment to be carried out on a patient. In particular, a treatment plan comprises information about pharmaceuticals to be given to the patient, for example about the type of pharmaceuticals and the dose in which they are to be applied. In case the medical treatment to be carried out comprises treatment by radiotherapy, a treatment plan in particular comprises information about the points in time and/or the time intervals at which radiotherapy sessions are to be conducted on the patient. In the case of radiotherapy treatment, the term of dose refers to a radiation dose caused by irradiation with in particular treatment radiation. Besides that, a radiotherapy treatment plan in particular comprises information about the kind of and dose (more particularly, the energy and time length of irradiation) of radiation to be applied. Furthermore, a radiotherapy treatment plan may comprise information about the location of the target region in the patient's body and the kind of disease from which the patient is suffering (such as the kind of tumour to be irradiated). In particular, a treatment plan for radiotherapy comprises information about the relative position between the target region and an arrangement of treatment beams. In general, a treatment plan may also comprise information about the anatomy or physiology of the patient, such as information about his height and weight, his gender, age and vital parameters (such as blood pressure, breathing frequency and heart rate). A radiotherapy treatment plan in particular comprises information about the treatment beam or treatment beams to be used, in particular by the arrangement of treatment beams. More particularly, a radiotherapy treatment plan comprises information about the positional arrangement of the arrangement of treatment beams, advantageously the position of the positional arrangement relative to the patient's body (in particular, relative to the target region, relative to healthy tissue or relative to critical structures). Preferably, the position of each beam line relative to the patient's body (or the aforementioned parts of the patient's body) is described by information contained in the treatment plan. Information describing the geometric relationship (i.e. the position or the positional arrangement relative to the patient's body and the positional arrangement itself) is in the framework of this disclosure also called patient-beam-relationship information.

In the following, the embodiment is described just as an example for the case that the candidate patient data are current patient data but can of course also be performed in the same manner if the candidate patient data are virtual patient data.

Preferably, current patient data comprising current patient information about a current patient's body is acquired. The current patient preferably is the patient on which the medical treatment described by the treatment plan is to be carried out. The treatment plan is thus also called a current treatment plan. The current patient information preferably comprises categories of information which describe medical information about the current patient. In particular, the medical information relates to anatomical, physiological or pathological information (also called current patient medical information) about the current patient. For example, the medical information describes the current patient's body dimensions (such as height or the geometry of specific body parts) or physiological parameters of the current patient's body (such as average blood pressure, heart rate or breathing rate) or pathological information (such as information about the patient's medical history or information about an illness or injury from which the current patient is suffering).

Preferably, reference treatment plan data comprising reference treatment plan information about a reference treatment plan is determined based on the current patient data. Preferably, the reference treatment plan has been drafted for patient data which fulfill specific conditions with respect to the current patient data. These conditions are described further below. Preferably, the reference treatment plan is predetermined and has been drafted to suit a medical treatment to be carried out on a reference patient. Information about the reference patient's body is preferably described by reference patient data and the reference treatment plan information has been generated preferably based on the reference patient data. The current patient and the reference patient may in a particular embodiment of the invention be identical which means that the current treatment plan is determined on a reference treatment plan which has also been generated for treatment of the current patient. This has the advantage that the medical history of the current patient can be used to determine the current treatment plan which may in some cases lead to a more patient-specific medical treatment. The reference treatment plan data is preferably stored as predetermined data in a database and comprises categories of information which comprise at least the categories of information described above with regard to the treatment plan in general.

Preferably, the current patient data comprises current target region data comprising current target region information about a target region in the current patient's body. (Of course, in case the candidate patient data are not current patient data but virtual patient data, the virtual patient data comprise information on the virtual target region which results after applying the first virtual treatment step (e.g. surgical resection step) to the current target region.) The target region preferably is a treatment body part, i.e. a part of the patient's body which is envisaged to be treated by the medical treatment, in particular by the treatment beam. Other regions of the patient's body which in particular are not part of a target region (i.e. outside body parts) are healthy regions (healthy tissue) and critical regions (critical tissue) which include the critical body parts. Healthy regions are commonly not to be treated by the medical treatment, however, an influence of the medical treatment on them is mostly inevitable but undesired.

This may for example be the case if the treatment has passed through healthy tissue on its way to the target region. Critical regions are such regions which shall not be influenced by the medical treatment. In particular, an influence of the medical treatment on critical regions has to be avoided. Examples of critical structures are vital organs such as the heart which shall not be influenced by specific pharmaceuticals or functional regions of the brain which shall not be irradiated by a treatment beam in order to avoid neurological effects caused by the medical treatment.

The current target region information in particular comprises categories of information which relate to the geometry, position or pathologic state of the target region. The term of geometry in this context encompasses for example the shape (for example similarity to a basic geometric shape such as a sphere or a box) or dimension (length, diameter, radius or circumference) of the target region. The position of the target region is in particular described by its position relative to other parts of the patient's body or relative to the treatment device in the context of this disclosure, a treatment device is the device used for emitting the treatment beam such as an x-ray tube, particle accelerator or radioactive substance. The pathologic state of the target region is in particular described by the kind of disease (more particularly, the type of tumour) or injury which is present in the target region. Additionally, the pathologic state may be described by the history of the disease or injury such as the geometry or the position of the target region at a previous point in time. The geometry of a target region may also be described by the volume or the two-dimensional area (both volume and area are also referred to as size) covered by the target region in a cross section or specific perspective.

Preferably, current treatment plan data is acquired by adapting the reference treatment plan data to the current patient data. The current treatment plan data preferably comprises current treatment plan information about the medical treatment to be carried out on the current patient. The current treatment plan information in particular is treatment plan information as described above in general with regard to a treatment plan. In particular, the reference treatment plan serves as a basis for generating the current treatment plan data. More particularly, the reference treatment plan information is adapted to the requirements of treating the current patient in view of the current patient information, in particular in view of anatomical and pathological information contained in the current patient information. Adapting the reference treatment plan information in particular comprises changing the reference treatment plan information such that a treatment plan is generated which is suitable to treat the current patient with the desired medical treatment.

Preferably, reference patient data comprising reference patient information about the reference patient's body is acquired. The reference patient information comprises categories of information selected at least from the above-described categories of information which may be contained in the current patient information. Preferably, the reference patient data comprises information, preferably image information, about the geometry of at least part of the reference patient's body. Preferably, the reference patient is the patient for whom the reference patient data and the reference treatment plan data have been generated. In particular, the reference treatment plan comprises information about a medical treatment to be carried out on the reference patient.

Preferably, the reference patient data comprises information, in particular image information, about the geometry of at least part of the reference patient's body. The respective image information is hereinforth also called reference patient image information (contained in reference patient image data) and current patient image information (contained in current patient image data). The reference patient image data and current patient image data are preferably acquired by application of a medical imaging method. The medical imaging method is in particular applied to the reference patient's body in order to acquire the reference patient image data and the current patient image data, respectively. Applying the medical imaging method in particular comprises acquiring image information which represents a cone beam computed tomography (CBCT) of at least part of the current patient's body and the reference patient's body, respectively.

Preferably, the reference patient data comprises reference target region data comprising reference target region information about a reference target region in the reference patient's body. The reference target region information describes categories of information in analogy to those described by the current target region information, however with regard to the reference patient's body if applicable.

Preferably, applicability data is determined based on the current patient data and the reference patient data. The applicability data preferably comprises applicability information about the applicability of the information contained in the reference patient data to the information contained in the current patient data. In the context of this disclosure, applicability in particular means the suitability of the information contained in the reference patient data with regard to the information contained in the current patient data in view of medical aspects. In particular, the applicability information describes a degree of similarity between the information contained in the reference patient data and information contained in the current patient data. In particular, the applicability data comprises or is determined based on information about whether or not the information contained in the reference patient data is applicable to the information contained in the current patient data. The degree of similarity between the information in the reference patient data and the information in the current patient data is preferably determined based on information about a measure of similarity, in particular a correlation, between the information in the reference patient data and the information in the current patient data. The applicability information preferably comprises information about the measure of similarity, in particular the applicability information is the measure of similarity.

Preferably, the applicability data is determined based on information about the position of critical structures in the current patient's body when compared information about the position of such critical structures in the reference patient's body. Depending on the distance between the respective positions, the measure of similarity on which the applicability information may be based can be determined. In particular, the position of the critical structure may be evaluated as a position relative to the current target region or the reference target region, respectively.

Preferably, the reference patient data is acquired based on assessing the result of elastically fusing geometry information about the geometry of at least part of the reference patient's body (also called reference patient geometry information) contained in the reference patient data to geometry information about the geometry of at least part of the current patient's body (also called current patient geometry information) contained in the current patient data. In particular, the reference patient data is acquired by elastically fusing the geometry information about the geometry of at least part of a plurality of reference patient's bodies contained in the corresponding plurality of reference patient datasets (which may be acquired within the disclosed method) to the geometry information about the geometry of at least part of the current patient's body. The parts of the respective bodies advantageously are the same anatomical structures. Then, a degree of fit of the fused reference patient geometry information fused to the current patient geometry information (also called fused geometry information) is determined. Depending on the degree of fit, i.e. the better the fit is and the smaller the differences are between the fused geometry information and the current patient geometry information, the reference patient data from which the reference patient geometry information has been acquired may be selected as the reference patient data to be used for the further steps of the method.

According to a preferable, more general embodiment, the applicability information comprises information about a geometric transformation between the current patient information and the reference patient information. In this case, the current patient information and the reference patient information in particular comprise geometric information about the anatomy of the current patient and the reference patient. The geometric transformation in particular is or comprises an elastic fusion and/or elastic fusion algorithm.

In this application, the term "image morphing" is also used as an alternative to the term "image fusion", but with the same meaning.

Elastic fusion transformations (e.g. image fusion transformation) are in particular designed to enable a seamless transition from one data set (e.g. first data set, e.g. first image) to another data set (e.g. second data set, e.g. second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighbouring voxels. Due in particular to a high number of (iteration) steps, large deformations can be implemented.

The determined elastic fusion transformation can be in particular used to determine a degree of similarity (similarity measure also referred to as "measure of similarity") between the first and second data set (first and second image). To this end, the deviation of the elastic fusion transformation and an identity transformation is determined. The degree of deviations can be for instance calculated by determining the difference between the determinant of the elastic fusion transformation and the identity transformation. The higher the deviation is the less is the similarity. Thus, the degree of deviation can be used to determine a measure of similarity.

A measure of similarity can in particular be determined on the basis of a determined correlation between the first and second data set.

Preferably, the current treatment plan data is determined based on the applicability data. For example, if the applicability information indicates that the reference treatment plan already fulfills the requirements for medical treatment of the current patient to a predetermined degree, the reference treatment plan data may be selected directly as the current treatment plan data without the need of further adaptation. If, however, the applicability information indicates a degree of similarity between the information contained in the reference patient data and the information in the current patient data, there will most likely exist a need of adaptation of the reference treatment plan information. In that case, determining the current treatment plan data preferably comprises adapting the reference treatment plan data based on the applicability data. The applicability data thus preferably also comprises information about how to adapt the reference treatment plan data in view of the medical treatment to be carried out on the current patient. Preferably, adapting the reference treatment plan data comprises applying a geometric transformation such as an elastic fusion algorithm to the reference treatment plan data. In particular, information about a positional arrangement or an arrangement of treatment beams described by the reference treatment plan information is elastically fused to the current patient geometry information.

Further preferably, the reference patient data comprises reference medical information in particular about the reference patient. The respective medical information preferably comprises at least one of anatomical, physiological and pathological information with regard to the respective patient as defined further above with regard to the current patient medical information.

Preferably, the current treatment plan data is determined by computing it on a cloud server. In particular, the reference treatment plan data is downloaded from a cloud server, for example to a local client computer. As part of adapting the reference treatment plan information, transformation data is then determined at the client computer, the transformation data comprising transformation information about the transformation from the reference treatment plan information to the current treatment plan information. Instead of computing the current treatment plan data at the client computer and uploading the correspondingly large amount of information to a cloud server, preferably only the transformation data is uploaded from the client computer to the cloud server in order to reduce data traffic between the two computers. The cloud server then uses the transformation information to adapt the reference treatment plan data which is still stored in the cloud. This allows to use the large computational capacities of a cloud server for conducting the computation of the expensive computation of the current treatment plan data.

Preferably, the transformation information describes a difference between the reference treatment plan information and the current treatment plan information. For example, the transformation information may describe only elements of the reference treatment plan information which may not be applied for conducting the medical treatment on the current patient. In particular, the transformation information describes a distortion embodied by a matrix transformation between the positional arrangement described by the reference treatment plan information and a positional arrangement to be described by the current treatment plan information, in particular a positional arrangement which has to be computed in order for the medical treatment to be feasible with regard to the current patient's needs. The transformation data is preferably determined based on the current patient data and the reference treatment plan data.

Preferably, the aforementioned current patient image data is acquired after the current patient has been put in place for medical treatment, in particular after the current patient has been placed on a bed on which he normally rests during radiotherapy. In particular, the current patient image data is acquired immediately before the medical treatment starts, in particular immediately before radiotherapy ensues.

The aforementioned measure of similarity described by the applicability information according to a preferred embodiment describes a similarity between the geometry of the current target region and the geometry of the reference target region. The term of geometry encompasses the same terminology as defined above with regard to the geometry of the current target region. In particular, the measure of similarity may in this case be acquired based on applying a three-dimensional subtraction algorithm with geometry information about the geometry of the current target region and geometry information about the geometry of the reference target region as inputs. Thereby, a difference between the two geometries, in particular a greater volume of one of the two target regions compared to the other one of the two target regions, can be determined. A subtraction algorithm essentially places predefined parts of image information over one another and outputs the difference or differences between the sets of image information (which are used as an input) with regard to one another.

Preferably, and in case the current patient is the reference patient, it is not necessary to determine the reference treatment plan data based on the reference patient data. Rather, the reference treatment plan data may be selected directly by a user who has knowledge of reference treatment plan data which has been generated specifically for treatment of the current patient. In case the current patient is the reference patient (i.e. is identical in person to the reference patient), the determined or selected reference treatment plan information in particular comprises information about the medical treatment previously applied to the current patient.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Preferably, the computer on which the aforementioned program is running is or comprises a cloud server.

The invention also encompasses a radiotherapy system comprising the aforementioned computer and a treatment device for treating a treatment body part of the current patient. The treatment device in particular comprises a treatment beam source for emitting a treatment beam. Furthermore, the radiotherapy system preferably comprises a beam source driver for changing the position of the treatment beam source. The beam source driver may for example comprise a motor and a mechanism which supports movement of the treatment beam source, in particular relative to the position of the patient (alternatively or additionally, the treatment beam source driver may be configured to move the patient relative to the position of the beam source).

The radiotherapy system preferably also comprises an analytical device constituted to generate at least one x-ray image of the current patient prior to applying the medical treatment to the patient. As mentioned before, the analytical device preferably comprises a CBCT device.

In order to verify that the current treatment plan information in fact is suitable for conducting the envisaged medical treatment on the current patient, the method described herein may also comprise steps of approving of the current treatment plan information. These steps are contained in the following further advantageous embodiments A to G which may be combined without prejudice with the above-described method of determining a treatment plan:

A. A method, in particular data processing method, of advantageously automatically approving of a treatment plan which describes a medical treatment to be carried out on a patient, the steps of the method being executed by a computer and comprising:
- acquiring approval template data comprising approval template information that describes an approval template containing acceptance and advantageously rejection criteria for current treatment plan information;
- determining criteria fulfillment data comprising criteria fulfillment information describing whether the current treatment plan information fulfils the criteria described by the approval template information or not; and
- accepting the current treatment plan information for carrying out the medical treatment on the patient if the criteria fulfillment information indicates that the current treatment plan information fulfils the criteria described by the approval template information, otherwise rejecting the current treatment plan information for further use in the medical treatment.

B. The method according to embodiment A, wherein the approval template information include information about a conformity index and/or a homogeneity index.

The term of conformity index describes a measure of how much of a projected surface or cross-section of the current target volume is covered by a treatment plan. The term of homogeneity index describes a measure of how (homogeneously) a dose applied to healthy tissue and critical structures is distributed over the patient's body or the respective healthy tissue and critical structures.

C. The method according to any one of embodiments A or B, wherein the approval template information includes information about a minimum dose to be applied to the current target region.

D. The method according to any one of embodiments A to C, wherein the approval template information includes information about a maximum dose to be applied to critical structures.

E. The method according to any one of embodiments A to D, wherein the approval template information includes information about a predetermined amount by which a dose distribution achieved when adapting geometry information about critical structures and the reference target volume to geometry information in the current patient data, may differ from a predefined dose distribution.

F. The method according to any one of embodiments A to E, wherein the approval template information comprises information about a predetermined threshold value by which a distortion of a positional arrangement of treatment beams caused by adapting information about the positional arrangement contained in the reference treatment plan information to geometry information contained in the current patient information may not exceed.

G. The method according to any one of embodiments A to F, wherein the approval template information is set independently for a minimum dose to be reached in the current target volume, a maximum dose to be reached in the target volume and a maximum dose to be reached in a critical structure.

END OF PART 1 OF AUTOMATIC TREATMENT PLANNING METHOD

In the following, example embodiments of the present invention are described as reference to the Figures which are merely to be regarded as examples of the invention without limiting the invention to these specific embodiments.

Figure 1:
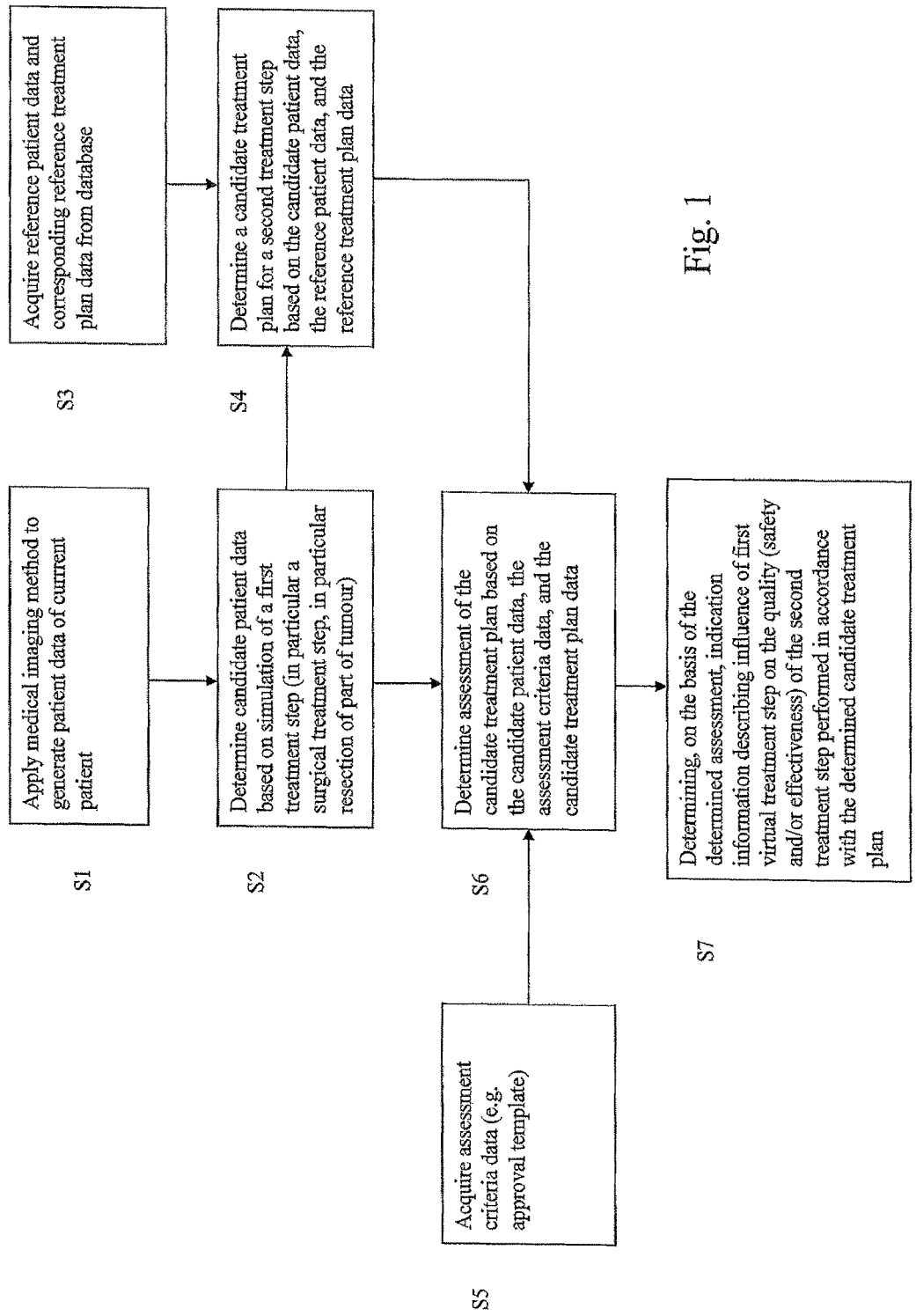
FIG. 1 shows an exemplary flow diagram of the method in accordance with the present invention.

FIG. 1 shows a flow diagram describing steps S1 to S7 which are performed in accordance with an exemplary embodiment of the treatment planning method according to the present invention. In a first step S1 a medical imaging method such as Mill and/or CT and/or CBCT is applied to generate patient data of a current patient. This patient data are processed in a step S2 in order to determine the candidate patient data. To this end, the candidate patient data are determined on the basis of simulation of a first treatment step. This first treatment step is in particular a surgical treatment step, in particular a step of resecting a part of the tumour. This step is a virtual surgical step and in particular a potential next step which can be performed by the surgeon. However, the surgeon is not aware if this step results in a geometry of the remaining tumour which is good enough for radiotherapy treatment (which is to be performed after surgery). The present invention allows in particular to determine if sufficient parts of the tumour have been resected so that the remaining parts of the tumour can be treated in high quality, in particular can be effectively and/or safely treated by radiotherapy. In particular, it can be checked if a further treatment step (i.e. one of the plurality of potential first treatment steps) results in a geometry of the tumour which allows for radiotherapy treatment of higher quality than a radiotherapy treatment of the tumour as it is in the current stage. In particular, it can be indicated to the surgeon that any further resection of the tumour does not result in a better outcome of the radiotherapy treatment. Such an indication can be given in the indication step S7 explained below.

According to step S3 reference patient data are acquired and corresponding reference treatment plan data are acquired from a database. Then in a step S4 a candidate treatment plan for a second treatment step is determined based on the candidate patient data, the reference patient data and the reference treatment plan data. The steps S3 and S4 are in particular explained in the second part entitled "automatic treatment planning method".

Furthermore, preferably in a step S5, assessment criteria data are acquired which describe in particular an approval template.

In a step S6, the information acquired in the steps S2, S4 and S5 are used to determine an assessment of the candidate treatment plan. In more detail, the assessment of the candidate treatment plan is based on the candidate patient data, the assessment criteria data, and the candidate treatment plan data. In particular, if the quality described by the determined assessment is above a predetermined threshold, this can be indicated to a user, in particular surgeon. He then is aware that the present status of the tumour is sufficient in order to achieve a good result with the radiotherapy. In this way, the surgeon is assisted in his decision whether to resect more of the tumour or not.

The quality described by the assessment can be indicated in a step S7. Furthermore, in a step S7, first virtual treatment steps can be indicated which can improve the quality of radiotherapy treatment after surgery.

Figure 2:
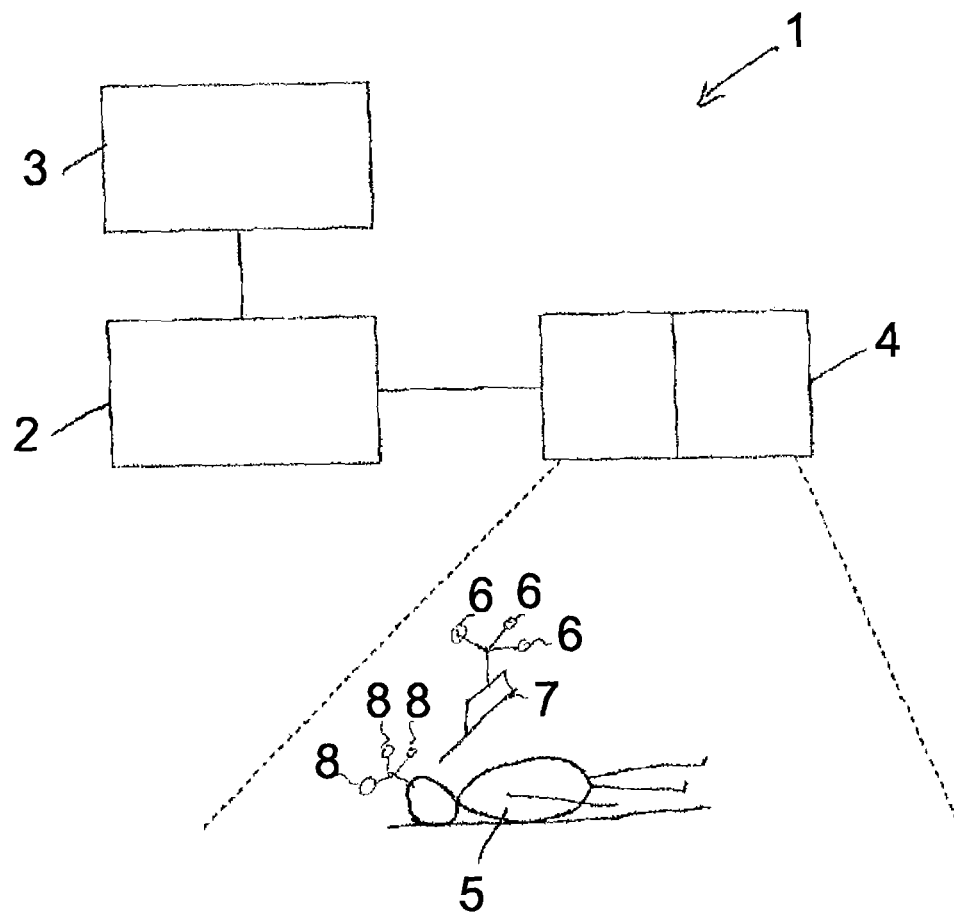
FIG. 2 shows an exemplary embodiment of the navigation system of the present invention.

FIG. 2 shows a navigation system 1). The navigation system 1) comprises a detector 4 (camera). The detector 4 is constituted to detect a marker device, in particular markers attached to a pointer and/or surgical instrument (for resecting parts of the tumour) and/or attached to the body of the patient 5. The markers of the marker device attached to the body are designated S8. The markers of the marker device attached to the pointer 7 are designed S6. A computer 2 performs a method of the present invention and in particular processes the signals detected by the detector 4 in order to determine the relative position between the instrument 7 (which can be a pointer or a surgical instrument) and part of the body (which is in particular the treatment body part). The computer calculates in particular if the surgical instrument is close a region, the resection of which results not in an improvement of the quality of radiotherapy treatment or even results in a reduction of quality in a later radiotherapy treatment.

The display 3 can in particular display regions of the tumour which, if resected, would result in an improvement or in a degradation of the quality of the radiotherapy treatment, if the radiotherapy treatment is performed after the surgery.

PART 2 OF AUTOMATIC TREATMENT PLANNING METHOD

Figure 3:
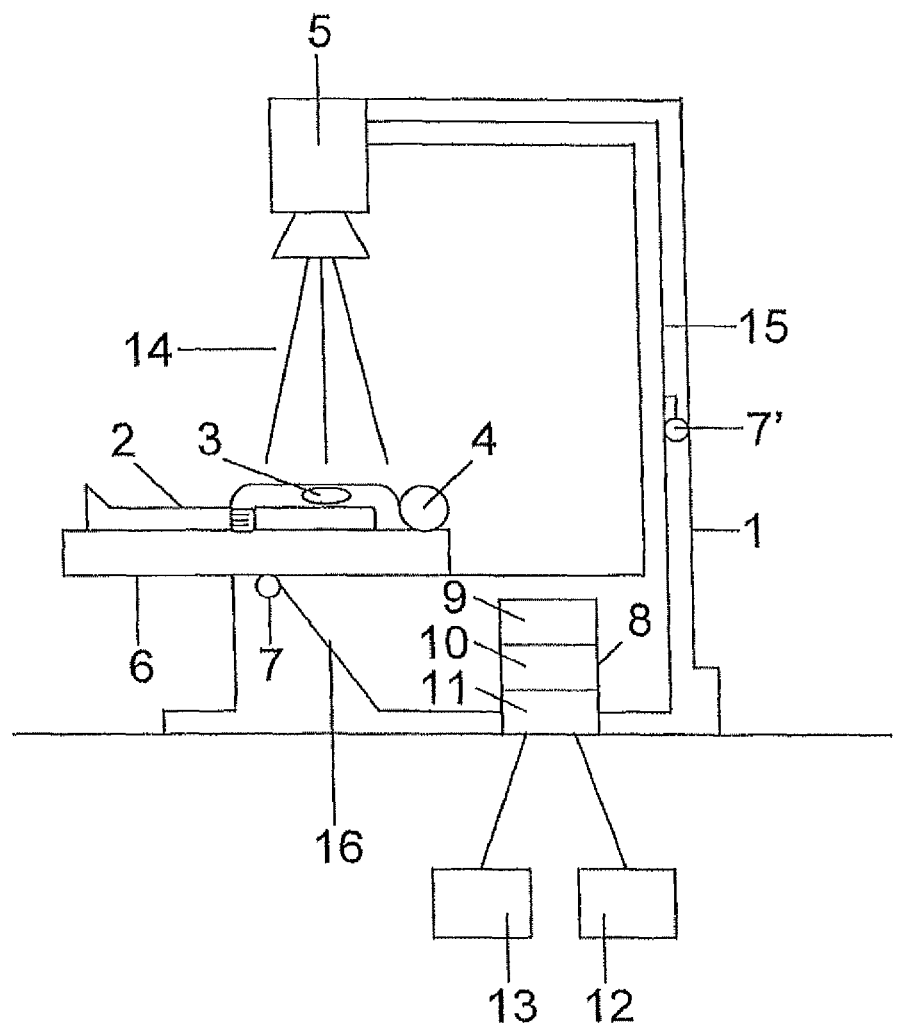
FIG. 3 shows a treatment setup as an example of a radiotherapy system with a patient's body placed ready for treatment by a treatment device.

As shown in FIG. 3, a patient's body 2 comprising a target region 3 and an off-target region 4 is placed on a patient couch 6 of a treatment device 1. The off-target region 4 comprises for example healthy tissue. The treatment device 1 comprises an irradiation portion 5 which is configured to take a CBCT image of the patient's body and to emit the treatment radiation 14. The treatment device 1 also comprises a motor 7 which is coupled to a transport mechanism of the couch 6 in order to move the patient's body 2 after it has been placed on the couch 6. The treatment device 1 also includes a computer 8 comprising a hard disc 9, a RAM 10 and a CPU 11. The computer 8 is connected by a data line 15 to the irradiation portion 5. The computer 8 is also connected to an input portion 13 and a display unit 12. The input portion 13 preferably comprises a keyboard and a pointing device such as a mouse or a joystick. The display unit 12 preferably comprises a graphic display device such as a monitor and an acoustic output device such as a loudspeaker. The computer 8 is also connected to the electric motor 7 via a data line 16 in order to automatically control the electric motor 7 in moving the couch 6. The treatment device 1 also comprises another electric motor 7' which is also connected to the computer 8 by the data line 15 and is designed to move, in particular shift and/or rotate, the irradiation portion 5 in an absolute co-ordinate system. The electric motor 7' can in particular move the irradiation portion 5 relative to the base of the treatment device 1 and/or relative to the absolute position of the couch 6 and therefore the patient's body 2 if it is placed on the couch 6. The electric motor 7' can in particular move the irradiation portion 5 relative to the base of the treatment device 1 and/or relative to the absolute position of the couch 6 and therefore the patient's body 2 if it is placed on the couch 6. Furthermore, the treatment device 1 is configured to vary other parameters of the beam, in particular the beam geometry (the shape of the beam), the number of beams, or the beam intensity.

The computer 8 is configured to execute the data processing method as described above by running the above-mentioned program.

Figure 4:
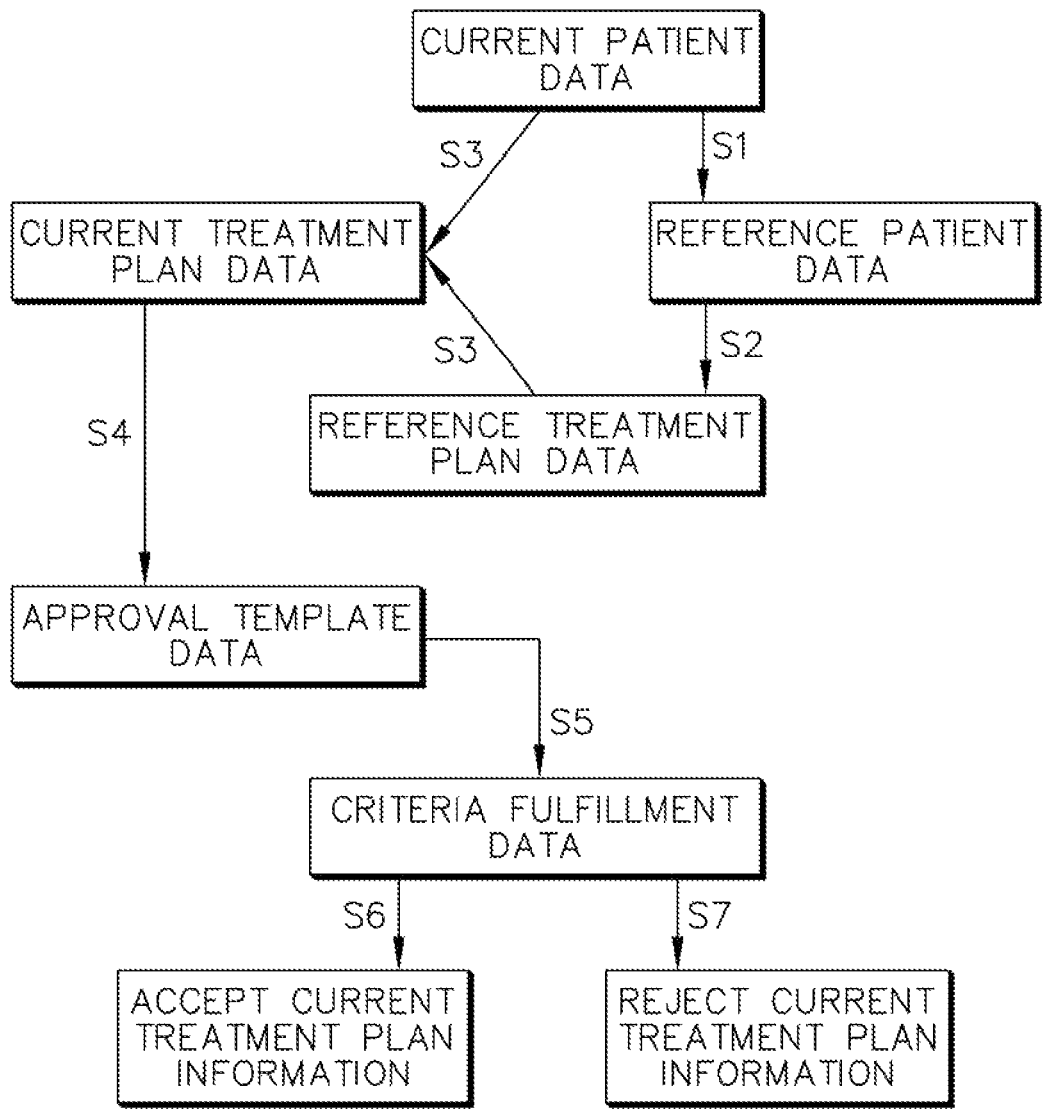
FIG. 4 is a flow diagram of an embodiment of the present invention.

FIG. 4 shows a flow diagram of a specific embodiment of the inventive method. After starting the method, the current patient data is acquired. In step S1, reference patient data which fulfills the above-described criteria of applicability to the current patient data is acquired. Based on the knowledge about the reference patient for whom the reference patient data was generated, step S2 continues with acquiring the reference treatment plan data. The reference treatment plan data is adapted to geometry information contained in the current patient data in order to determine the current treatment plan data in step S3. In step S4, the approval template data is acquired and step S5 continues with comparing the current treatment plan information to the approval template information contained in the approval template data. The result of the comparison is output as criteria fulfillment data. If the comparison results in that the acceptance criteria of the approval template information are fulfilled, the current treatment plan information is accepted in step S6. If it is concluded that the current treatment plan information does not fulfill the fulfillment criteria or fulfills rejection criteria (if the latter are contained in the approval template information), the current treatment plan information is rejected in step S7. In that case, the inventive method may return to its start and for a new run of the search for reference patient data which fulfill the applicability criteria described above in the manner next best to the manner in which the reference patient data previously acquired fulfilled the applicability criteria.

If the fulfillment criteria information comprises information about minimum or maximum dose values to be achieved, for example, in the current target region, a simulation of a radiotherapy session based on the current treatment plan information and the current patient information may provide image data from which an absorption coefficient in specific tissue of the patient's body may be determined, in particular by using the concept of Hounsfield units. Thereby, it may be determined whether the radiation therapy parameters contained in the current treatment plan information are acceptable in view of the dose parameters described by the approval template information.

END OF PART 2

In particular, the invention further relates to the following embodiments which are parts of the description. Advantageous features of the different embodiments can be combined with each other in one embodiment. It is further possible to omit one or more features from a specific embodiment. The omitted one or more features are not necessary for the specific embodiment.

Preferred embodiments and/or features of the invention are indicated as follows:

A. data processing method for determining an assessment of a candidate treatment plan, the candidate treatment plan being a plan for treatment of a patient's body, the data processing method comprising the following steps which are in particular performed by a computer:
  a). acquiring candidate patient data describing medical information on the patient;
  b). acquiring assessment criteria data describing criteria for assessing a treatment plan to be assessed and referred to as assessable treatment plan;
  c). acquiring candidate treatment plan data describing the candidate treatment plan; and
  d). determining the assessment of the candidate treatment plan on the basis of the candidate patient data, the assessment criteria data, and the candidate treatment plan data.

B. The data processing method of the previous embodiment, wherein the assessment describes a quality of the candidate treatment plan.

C. The data processing method of one of the previous embodiments, wherein the candidate patient data describe current patient data which describe the current medical status of the patient.

D. The data processing method of the preceding embodiment, wherein the candidate treatment plan is determined based on the current patient data for treating the patient which is in the current medical status.

E. The data processing method of the preceding embodiment as far as depending from the claim which first mentions the quality of the candidate treatment plan, comprising the step of determining whether the quality is above a predetermined threshold.

F. The data processing method according to the preceding embodiment comprising determining indication information describing that the quality is above the predetermined threshold.

G. The data processing method of one of the previous embodiment, wherein the candidate patient data are virtual patient data.

H. The data processing method of the previous embodiment, wherein the virtual patient data are determined based on a simulation of a first virtual treatment of the patient by determining the effect of the first virtual treatment of the patient on the current patient data.

I. The data processing method of the preceding embodiment, wherein the first virtual treatment is a surgical treatment.

J. The data processing method of one of the two directly preceding embodiments, wherein the step of acquiring the candidate treatment plan data comprises determining the candidate treatment plan data on the basis of the virtual patient data.

K. The data processing method of the previous embodiment, wherein the determined candidate treatment plan describes a plan for a treatment of the patient according to a second virtual treatment.

L. The data processing method of the preceding embodiment, wherein the second virtual treatment is a radiotherapy treatment.

M. The data processing method of the one of the two directly preceding embodiments, further comprising the step of acquiring a plurality of first virtual treatment data describing a plurality of first virtual treatments, respective ones of the plurality of virtual treatment data describing a respective one of the first virtual treatments;

wherein the step of determining the virtual patient data comprises determining a plurality of the virtual patient data based on the described plurality of the first virtual treatments, respective ones of the plurality of the virtual patient data being determined based on a respective one of the plurality of first virtual treatments;

wherein the step of determining the candidate treatment plan data comprises determining a plurality of the candidate treatment plan data respectively describing one of a plurality of assessable treatment plans, a respective one of the plurality of the candidate treatment plans being determined based on a respective one of the plurality of the virtual patient data; and wherein the step of determining the assessment comprises determining a plurality of the assessments on the basis of the determined plurality of candidate treatment plans, the virtual patient data and the assessment criteria data, a respective one of the plurality of the assessments being determined on the basis of a respective one of the plurality of candidate treatment plans, the virtual patient data and the assessment criteria data.

N. The data processing method of the preceding embodiment comprising, based on the plurality of the determined assessments, determining one of the plurality of the treatment plans for which the assessment indicates best quality and/or that one of the first virtual treatments based on which the one of the plurality of the treatments plans was determined for which the assessment indicates the best quality.

O. The data processing method of one of the two directly preceding embodiments, wherein a respective one of the plurality of assessments is assigned to a respective one of the plurality of first virtual treatments based on which the respective one of the plurality of assessments has been determined.

P. The data processing method of one of the preceding embodiments, comprising: acquiring region data which describe a link between regions of the patient's body and the first virtual treatments; and
  respectively determining for the regions a quality of the first virtual treatment based on the assigned assessment and/or determining whether the quality is above a predetermined threshold and/or determining whether the quality improves compared to the case that no first virtual treatment is performed.

Q. The data processing method of one of the previous embodiments, wherein the treatment plan describes a radiotherapy treatment which is planned to be performed for treating a target region of the patient.

R. The data processing method of one of the previous embodiments, wherein the candidate position data comprise information on the target region.

S. The data processing method of the previous embodiment, wherein the information on the target region comprises information on the geometry and/or position of the target region.

T. The data processing method of the previous embodiment, wherein the information on the geometry describes the size and/or shape and/or volume of the target region.

U. The data processing method of one of the previous embodiments, wherein the candidate patient data comprise information which is generated by using medical imaging methods for analyzing the patient for generating image data of the anatomical structure of the patient.

V. The data processing method of one of the preceding embodiments, wherein the candidate patient data are at least partly determined based on determining the geometry and/or position of invisible body parts based on the geometry and/or position of visible body parts, visible body parts being parts identifiable in image data generated by a medical imaging method and invisible body parts being parts which cannot be identified in the image data.

W. The data processing method of the previous embodiments, wherein the candidate treatment plan is determined only based on MRI data.

X. The data processing method of one of the previous embodiments as far as depending from the claim which first mentions the target region, wherein the treatment plan is usable for at least a partial treatment of the target region.

Y. The data processing method of one of the previous embodiments, wherein the candidate treatment plan describes an arrangement of treatment beams.

Z. The data processing method of one of the previous embodiments, wherein the assessment criteria data describe at least one approval template which describes the criteria for assessing the assessable treatment plan.

AA. The data processing method of one of the previous embodiments, wherein the criteria comprise acceptance and/or rejection criteria for the assessable treatment plan.

BB. The data processing method of one of the previous embodiments, wherein the criteria comprise predetermined criteria and/or criteria determined based on the candidate patient data.

CC. The data processing method of one of the preceding embodiments, wherein the assessment criteria data comprise a criteria table which assigns different criteria to different reference patient data and wherein that one of the different criteria is selected for the assessment which is assigned to that one of the reference patient data which has highest similarity to the candidate patient data.

DD. The data processing method of one of the preceding embodiments as far as depending on the claim which first mentions the approval template, wherein the approval template is adapted based on the candidate patient data.

EE. The data processing method of one of the preceding embodiments, wherein the criteria describe a required coverage of the target region by the treatment beam and/or by a minimum dose level.

FF. The data processing method of one of the preceding embodiments, wherein the criteria describe a required homogeneity for the dose distribution in parts outside the target region.

GG. The data processing method of one of the preceding embodiments, wherein the criteria describe a minimum dose limit for the target region.

HH. The data processing method of one of the preceding embodiments, wherein the criteria describe a maximum dose limit for the parts outside the target region, in particular for critical body parts.

II. The data processing method of one of the preceding embodiments as far as depending from the claim which first mentions the approval template, wherein the approval template describes a dose distribution.

JJ. The data processing method of the preceding embodiment wherein the approval template describes criteria for maximum deviation from the described dose distribution which is still allowed.

KK. The data processing method according to one of the two directly preceding embodiments, wherein a deviation from the dose distribution is described as a distortion which may not exceed a predefined threshold.

LL. The data processing method of one of the preceding embodiments, wherein the criteria are independently set for the level of underdosage within the target volume, the maximum dose around the tumour, and the maximum dose for each critical structure.

MM. The data processing method of one of the preceding embodiments, wherein there is a plurality of criteria which are weighted using a balanced score card.

NN. The data processing method of one of the previous embodiments, wherein dose distribution data are acquired which describe the dose distribution within the patient's body if a radiotherapy treatment is performed in accordance with the candidate treatment plan.

OO. The data processing method of the previous embodiment, wherein the acquired assessment criteria comprise criteria for the dose distribution and wherein the determining of the assessment is based on the dose distribution described by the dose distribution data.

PP. The data processing method of one of the preceding embodiments, wherein the candidate patient data comprise data referred to as treatment beam absorption data, the treatment beam absorption data describing absorption properties of at least part of the patient's body to be treated in accordance with the candidate treatment plan or wherein treatment beam absorption data are determined from the reference patient data which are most similar to the candidate patient data, in particular wherein for the determination a statistical processing of the reference patient data is performed, wherein as far as the claim depends on the preceding claims, the dose distribution data are determined based on the treatment beam absorption data and the candidate treatment plan.

QQ. The data processing method of one of the preceding embodiments, wherein comparison dose distribution data are acquired which describe comparison dose distributions for patients referred to as comparison patients which have been treated in accordance with treatment plans referred to as comparison treatment plans and wherein the dose distribution is determined based on similarity between the candidate treatment plan and the comparison treatment plans and/or similarity between the candidate patient data and patient data which describe the comparison patients.

RR. The data processing method of the preceding embodiment, wherein the determination of the dose distribution based on the comparison dose distributions uses statistical procedures which process the comparison dose distributions described by the comparison dose distribution data.

SS. The data processing method of the previous embodiment, wherein dose distribution within the patient's body is calculated based on the treatment beam absorption data and the candidate treatment plan data and wherein the fulfillment of the criteria is decided based on the determined dose distribution.

TT. The data processing method of the previous embodiment, wherein the criteria describe a dose volume histogram referred to as target dose volume histogram and criteria which describe a maximum allowed deviation from the target volume histogram.

UU. The data processing method of one of the preceding embodiments, wherein the determined assessment describes safety and/or effectiveness of a treatment performed in accordance with the candidate treatment plan.

VV. The data processing method of one of the preceding embodiments, wherein the step of acquiring the candidate treatment plan data comprises determining the candidate treatment plan data on the basis of the candidate patient data or comprises receiving predetermined treatment plan data which were predetermined for the treatment, in particular radiotherapy treatment of the patient, in particular the radiotherapy treatment of the target region.

WW. The data processing method of one of the preceding embodiments further comprising the step of acquiring reference patient data comprising reference data information about the reference target region of a reference patient's body.

XX. The data processing method of one of the two directly preceding embodiments comprising:
  determining, based on the candidate patient data, reference treatment plan data comprising reference treatment plan information about a reference treatment plan.

YY. The method according to one of the preceding embodiments as far as depending from the claim which first mentions the reference treatment plan data, wherein determining the candidate treatment plan data comprises adapting the reference treatment plan data based on the candidate patient data or selecting the reference treatment plan data as current treatment plan data.

ZZ. The method according to one of the preceding embodiments as far as depending from the claim which first mentions the reference patient information, wherein the reference patient data comprises information, preferably image information, about the geometry of at least part of the reference patient's body and wherein the candidate patient data comprises information, preferably image information, about the geometry of at least part of the candidate patient's body.

AAA. The method according to any one of the preceding embodiments as far as depending on the claim which first mentions the reference patient data, comprising:
  determining, based on the candidate patient data and the reference patient data, applicability data comprising applicability information about the applicability of the information contained in the reference patient data to the information contained in the candidate patient data.

BBB. The method according to the preceding embodiment, wherein the applicability data comprises or is determined based on information about whether or not the information contained in the reference patient data is applicable to the information contained in the candidate patient data.

CCC. The method according to any one of the two preceding embodiments, wherein the applicability data is information about a measure of similarity, in particular a correlation, between information in the reference patient data and information in the candidate patient data or is determined based on the information about the measure of similarity.

DDD. The method according to any one of the preceding embodiments, wherein the reference patient data is acquired based on assessing the result of elastically fusing geometry information about the geometry of at least part of the reference patient's body contained in the reference patient data to geometry information about the geometry of at least part of the current patient's body contained in the current patient data.

EEE. The method according to any one of the four preceding embodiments, wherein the applicability data is determined based on information about the position of critical structures in the current patient body, in particular relative to the current target region, or in the reference patient body, in particular relative to the reference target region.

FFF. The method according to any one of the five preceding embodiments, wherein the applicability information comprises information about a geometric transformation, in particular an elastic fusion, between the current patient information and the reference patient information.

GGG. The method according to the preceding claim as far as dependent on the embodiment which first mentions the applicability data, wherein the candidate treatment plan data is determined based on the applicability data.

HHH. The method according to the preceding embodiment, wherein determining the candidate treatment plan data comprises adapting the reference treatment plan data based on the applicability data.

III. The method according to any one of the preceding embodiments, wherein the candidate patient data comprises information about spatial characteristics of the current target region, in particular the geometry or position of the current target region.

JJJ. The method according to any one of the preceding embodiments as far as depending on the claim which first mentions the reference patient data, wherein the candidate patient data comprises candidate patient medical information about the candidate patient and wherein the reference patient data comprises reference medical information in particular about the reference patient.

KKK. The method according to the preceding embodiment, wherein the medical information comprises anatomical, physiological or pathological information.

LLL. The method according to the preceding embodiment as far as dependent on the claim which first mentions the reference treatment plan data, wherein adapting the reference treatment plan data comprises applying an elastic fusion algorithm to the reference treatment plan data.

MMM. The method according to the preceding embodiment, wherein the reference treatment plan data comprises information about a positional arrangement of treatment beams and wherein adapting the reference treatment plan comprises changing the positional arrangement of an arrangement of treatment beams described by the reference treatment plan information based on applying the elastic fusion algorithm to the reference treatment plan data.

NNN. The method according to the one of the preceding embodiments as far as depending from the claim which first mentions the reference treatment plan data, wherein current treatment plan data is determined by computing it on a cloud server, wherein the reference treatment plan data is downloaded from a cloud server and transformation data comprising transformation information about a transformation from the reference treatment plan information to the candidate treatment plan information is uploaded to the cloud server for computation of the candidate treatment plan data.

OOO. The method according to the preceding embodiment, wherein the transformation information describes a difference between the reference treatment plan information and the candidate treatment plan information.

PPP. The method according to one of the two directly preceding embodiments, wherein the transformation information describes a distortion matrix between the positional arrangement described by the reference treatment plan information and a positional arrangement to be described by the current treatment plan information.

QQQ. The method according to any one of the preceding embodiments as far as depending from the claim which first mentions the reference patient data, wherein the candidate patient data comprises candidate patient image data and wherein the reference patient data comprises reference patient image data, the candidate patient image data and the reference patient image data acquired by application of a medical imaging method.

RRR. The method according to the preceding embodiment, wherein the application of a medical imaging method comprises acquiring image information representing a cone beam computed tomography of at least part of the current patient's body and the reference patient's body.

SSS. The method according to the preceding embodiment, wherein the candidate patient image data is acquired after the current patient has been put in place for medical treatment, in particular immediately before the medical treatment starts.

TTT. The method according to any one of the preceding embodiments as far as dependent on the claim which first mentions the applicability data, wherein the applicability data comprises information about a measure of similarity between the geometry of the candidate target region and the geometry of the reference target region.

UUU. The method according to the preceding embodiment, wherein the measure of similarity is acquired based on applying a three-dimensional subtraction algorithm.

VVV. The method according to any one of the preceding embodiments as far as dependent on the claim which first mentions the reference patient, wherein the candidate patient is the reference patient.

WWW. The method according to the preceding embodiment, wherein the reference treatment plan data has been generated specifically for treatment of the candidate patient, wherein the reference treatment plan information in particular comprises information about a medical treatment previously applied to the candidate patient.

XXX. The data processing method of one of the preceding embodiments comprising the step of determining indication information which describes the determined assessment.

YYY. The data processing method of one of the preceding embodiments as far as depending on the claim which first mentions the first virtual treatment, wherein the first virtual treatment of the patient which results in the candidate treatment plan having the best assessment is determined.

ZZZ. The data processing method of one of the preceding embodiments as far as depending on the claim which first mentions the first virtual treatment, wherein indication information is determined which describes the best first virtual treatment.

AAAA. The data processing method of one of the preceding embodiments as far as depending on the claim which first mentions the first virtual treatment, wherein indication information is determined which describe at least one first virtual treatment, in particular a virtual surgery step which results in candidate patient data which in turn result in a determined assessment which is acceptable according to the assessment criteria data.

BBBB. The data processing method of one of the preceding embodiments, wherein at least part of the steps of the method are performed on a cloud server.

CCCC. The data processing method of one of the preceding embodiments comprising the step of acquiring instrument data, the instrument data describing the position of an instrument relative to the target region.

DDDD. The data processing method of the preceding embodiments comprising the step of acquiring instrument criteria data which describe criteria for allowed positions for allowed or not allowed positions of the instrument.

EEEE. The data processing method according to the preceding embodiment, wherein the instrument criteria data are determined based on first virtual treatment steps, in particular virtual surgical treatment step which result in a negative assessment of the candidate treatment plan determined for the first virtual treatment step and/or determined based on first virtual treatment steps, in particular virtual surgical treatment step which result in a positive assessment of the candidate treatment plan determined for the first virtual treatment step.

FFFF. A program which, when running on a computer or when loaded onto a computer, causes the computer to perform one or more or all of the method steps according to any one of the preceding embodiments and/or a program storage medium on which the program is stored in particular in a non-transitory form and/or a computer on which the program is running or into the memory of which the program is loaded and/or a signal wave, in particular a digital signal wave, carrying information which represents the program, in particular the aforementioned program, which in particular comprises code means which are adapted to perform any or all of the method steps described herein.

GGGG. The computer according to the preceding embodiment, wherein the computer comprises a cloud server.

HHRH. A navigation system, comprising:
the computer according to anyone of the directly two preceding embodiments;
a detection device for detecting the position of a surgical instrument.

IIII. The navigation system of the preceding embodiment, wherein the computer is constituted to generate signals which indicate whether the position of the instrument is close to and/or within a and/or moving towards a region of the patient's body which is determined to be preferred or less-preferred for a resection step based on the determined assessment.

JJJJ. The navigation system of one of the two directly preceding embodiments wherein the computer is constituted to generate display signals for indication of preferred or less-preferred regions of the patient's body for a resection step.

The invention claimed is:

1. A computer implemented method, comprising:
acquiring current patient data from a patient, the current patient data describing medical information generated by medical examination of the patient and describing a medical status of the patient;
determining simulated patient data based on a simulation of a first medical treatment step of the patient by determining an effect of the simulation of the first medical treatment step on the current patient data;
acquiring second medical treatment step data describing a second medical treatment step which is a potential second medical treatment step to be performed after the first medical treatment step;
acquiring assessment criteria data describing criteria for assessing the second medical treatment step;
automatically determining an assessment of the second medical treatment step by processing the simulated patient data, the assessment criteria data, and the second medical treatment step data by a computer;
wherein the acquiring the second medical treatment step data includes determining the second medical treatment step data based on the simulated patient data; and
providing for presentation to a medical user an indication based on the determined assessment of the second medical treatment step.

2. The method of claim 1, further comprising indicating a quality described by the determined assessment to the medical user.

3. The method of claim 1, wherein the current patient data are medical examination data which comprise medical image data generated by an apparatus-based medical imaging method, wherein the medical imaging method is to generate image data of an anatomical structure of the patient.

4. The method of claim 1, wherein the medical information described by the current patient data comprises at least one of anatomical, physiological or pathological information.

5. The method of claim 1, wherein the indication indicates influence of the first medical treatment step on a quality of the second medical treatment step.

6. The method of claim 1, wherein at least one of the first medical treatment step or the second medical treatment step is at least one of a pharmaceutical treatment, a radiotherapy treatment or a surgical treatment.

7. The method of claim 6, wherein the first medical treatment step is a surgical resection for removing part of an anatomical structure of the patient.

8. The method of claim 6, wherein the second medical treatment step is a radiotherapy treatment.

9. The method of claim 1, further comprising:
acquiring a plurality of first medical treatment step data describing a plurality of first medical treatment steps, respective ones of a plurality of simulated treatment data describing a respective one of the plurality of first medical treatment steps;
wherein the determining the simulated patient data comprises determining a plurality of the simulated patient data based on the plurality of first medical treatment step data, respective ones of the plurality of the simulated patient data being determined based on a respective one of the plurality of first medical treatment steps;
wherein determining the second medical treatment step data comprises determining a plurality of the second medical treatment step data respectively describing one of a plurality of second medical treatment steps, a respective one of the plurality of the second medical treatment step data being determined based on a respective one of the plurality of the simulated patient data; and
wherein the determining the assessment of the second medical treatment step comprises determining a plurality of assessments on the basis of the determined plurality of second medical treatment step data, the simulated patient data and the assessment criteria data, a respective one of the plurality of assessments being determined on the basis of a respective one of the plurality of second medical treatment steps, the simulated patient data and the assessment criteria data.

10. The method of claim 9, further comprising determining that one of the plurality of first medical treatment steps based on which one of the plurality of second medical treatment steps was determined for which the assessment indicated best quality.

11. The method of claim 1, further comprising:
acquiring region data which describe a link between regions of a patient's body and the first medical treatment step; and
respectively determining for the regions a quality of the first medical treatment step based on an assigned assessment.

12. The method of claim 11, further comprising respectively determining whether the respectively determined quality is above a predetermined threshold.

13. The method of claim 11, further comprising respectively determining whether the quality improves compared to a case that no first treatment step is performed.

14. The method of claim 1, wherein the assessment criteria data comprise a criteria table which assigns different criteria to different reference patient data and wherein, out of the different criteria, one is selected for assessment which is assigned to one of the reference patient data which has highest similarity to the current patient data.

15. The method of claim 1, further comprising:
determining indication information for the indication, the indication information describing at least one simulation of the first medical treatment step which results in a determined assessment which is acceptable according to the assessment criteria data; and
wherein a determined acceptable quality for providing the indication to a medical doctor is based upon determined simulated patient data.

16. The method of claim 1, further comprising:
acquiring instrument criteria data which describe criteria for allowed positions of an instrument used for the first medical treatment step or for not allowed positions of the instrument;
wherein the instrument criteria data are determined based on a first simulation of the first medical treatment step which results in a negative assessment of the second medical treatment step determined for the simulation of the first medical treatment step and/or based on a second simulation of the first medical treatment step which results in a positive assessment of the second medical treatment step determined for the simulation of the first medical treatment step; and
wherein, based on the determined instrument criteria data as well as instrument data which describes a position of the instrument used for the first medical treatment step, indication information for a medical doctor is determined to provide an indication indicating whether the instrument is close to a region, a first medical treatment of which may improve or not improve or reduce a quality of the second medical treatment step.

17. The method of claim 1, wherein the indication indicates that a quality of the second medical treatment step described by the assessment of the second medical treatment step is above a predetermined threshold.

18. A system, comprising:
a computing device having at least one or more processors and associated memory, the memory storing instructions that, when executed by the at least one or more processors, cause the at least one or more processors to:
acquire current patient data from a patient, the current patient data describing medical information generated by medical examination of the patient and describing a medical status of the patient;
determine simulated patient data based on a simulation of a first medical treatment step of the patient by determining an effect of the simulation of the first medical treatment step on the current patient data;
acquire second medical treatment step data describing a second medical treatment step which is a potential second medical treatment step of radiotherapy for later treatment of the patient to be performed after the first medical treatment step;
acquire assessment criteria data describing criteria for assessing the second medical treatment step;
automatically determine an assessment of the second medical treatment step by processing the simulated patient data, the assessment criteria data, and the second medical treatment step data by a computer;

wherein the acquiring the second medical treatment step data includes determining the second medical treatment step data based on the simulated patient data; and provide for presentation to a medical user an indication based on the determined assessment of the second medical treatment step.

19. A non-transitory computer-readable storage medium storing computer instructions executable by one or more processors to:

acquire, by the one or more processors, current patient data describing medical information generated by medical examination of a patient and describing a medical status of the patient;

determine simulated patient data, by the one or more processors, based on a simulation of a first medical treatment step of the patient by determining an effect of the simulation of the first medical treatment step on the current patient data;

acquire, by the one or more processors, second medical treatment step data describing a second medical treatment step which is a potential second medical treatment step to be performed after the first medical treatment step;

acquire, by the one or more processors, assessment criteria data describing criteria for assessing the second medical treatment step;

automatically determine, by the one or more processors, an assessment of the second medical treatment step by processing the simulated patient data, the assessment criteria data, and the second medical treatment step data;

wherein the acquiring the second medical treatment step data includes determining, by the one or more processors, the second medical treatment step data based on the simulated patient data; and provide for presentation to a medical user an indication indicating influence of the first medical treatment step on a quality of the second medical treatment step.

20. A computer implemented method, comprising:

acquiring current patient data from a patient, the current patient data describing medical information generated by medical examination of the patient and describing a medical status of the patient;

determining simulated patient data based on a simulation of a first medical treatment step of the patient by determining an effect of the simulation of the first medical treatment step on the current patient data;

wherein the first medical treatment step is a surgical resection for removing part of an anatomical structure of the patient;

acquiring second medical treatment step data describing a second medical treatment step which is a potential second medical treatment step to be performed after the first medical treatment step;

wherein the second medical treatment step is a radiotherapy treatment;

wherein the acquiring the second medical treatment step data includes determining the second medical treatment step data based on the simulated patient data;

acquiring assessment criteria data describing criteria for assessing the second medical treatment step;

automatically determining an assessment of the second medical treatment step by processing the simulated patient data, the assessment criteria data, and the second medical treatment step data by a computer; and providing for presentation to a medical user an indication based on the determined assessment of the second medical treatment step.

21. A system, comprising a computing device having at least one or more processors and associated memory, the memory storing instructions that, when executed by the at least one or more processors, cause the at least one or more processors to:

acquire current patient data from a patient, the current patient data describing medical information generated by medical examination of the patient and describing a medical status of the patient;

determine simulated patient data based on a simulation of a first medical treatment step of the patient by determining an effect of the simulation of the first medical treatment step on the current patient data;

wherein the first medical treatment step is a surgical resection for removing part of an anatomical structure of the patient;

acquire second medical treatment step data describing a second medical treatment step which is a potential second medical treatment step to be performed after the first medical treatment step;

wherein the second medical treatment step is a radiotherapy treatment;

wherein the acquiring the second medical treatment step data includes determining the second medical treatment step data based on the simulated patient data;

acquire assessment criteria data describing criteria for assessing the second medical treatment step;

automatically determine an assessment of the second medical treatment step by processing the simulated patient data, the assessment criteria data, and the second medical treatment step data by a computer; and provide for presentation to a medical user an indication based on the determined assessment of the second medical treatment step.

22. A non-transitory computer-readable storage medium storing computer instructions executable by one or more processors to perform a computer implemented method of:

acquiring current patient data from a patient, the current patient data describing medical information generated by medical examination of the patient and describing a medical status of the patient;

determining simulated patient data based on a simulation of a first medical treatment step of the patient by determining an effect of the simulation of the first medical treatment step on the current patient data;

wherein the first medical treatment step is a surgical resection for removing part of an anatomical structure of the patient;

acquiring second medical treatment step data describing a second medical treatment step which is a potential second medical treatment step to be performed after the first medical treatment step;

wherein the second medical treatment step is a radiotherapy treatment;

wherein the acquiring the second medical treatment step data includes determining the second medical treatment step data based on the simulated patient data;

acquiring assessment criteria data describing criteria for assessing the second medical treatment step;

automatically determining an assessment of the second medical treatment step by processing the simulated patient data, the assessment criteria data, and the second medical treatment step data by a computer; and providing for presentation to a medical user an indication based on the determined assessment of the second medical treatment step.

\* \* \* \* \*